United States Patent
Slayton et al.

(10) Patent No.: US 9,827,450 B2
(45) Date of Patent: Nov. 28, 2017

(54) SYSTEM AND METHOD FOR FAT AND CELLULITE REDUCTION

(71) Applicant: Guided Therapy Systems, LLC, Mesa, AZ (US)

(72) Inventors: Michael H. Slayton, Tempe, AZ (US); Peter G. Barthe, Phoenix, AZ (US); Inder Raj S. Makin, Mesa, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 0 days.

(21) Appl. No.: 15/650,246

(22) Filed: Jul. 14, 2017

(65) Prior Publication Data

US 2017/0312551 A1 Nov. 2, 2017

Related U.S. Application Data

(63) Continuation of application No. 15/374,918, filed on Dec. 9, 2016, now Pat. No. 9,707,412, which is a
(Continued)

(51) Int. Cl.
*A61N 7/02* (2006.01)
*A61B 8/00* (2006.01)
(Continued)

(52) U.S. Cl.
CPC .................. *A61N 7/02* (2013.01); *A61B 8/14* (2013.01); *A61B 8/429* (2013.01); *A61B 8/4483* (2013.01);
(Continued)

(58) Field of Classification Search
CPC .... A61N 7/02; A61N 7/00; A61N 2007/0008; A61B 8/14; A61B 8/4455; A61B 8/429;
(Continued)

(56) References Cited

U.S. PATENT DOCUMENTS

| 2,427,348 A | 9/1947 | Bond et al. |
| 2,792,829 A | 2/1952 | Calosi |

(Continued)

FOREIGN PATENT DOCUMENTS

| CN | 104027893 | 9/2014 |
| DE | 4029175 | 3/1992 |
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |

(Continued)

OTHER PUBLICATIONS

U.S. Appl. No. 12/996,616, filed Jan. 12, 2011, Hand Wand for Ultrasonic Cosmetic Treatment and Imaging.
(Continued)

*Primary Examiner* — Bo J Peng
(74) *Attorney, Agent, or Firm* — Knobbe Martens Olson & BEar LLP

(57) ABSTRACT

A method and system for providing ultrasound treatment to a tissue that contains a lower part of dermis and proximal protrusions of fat lobuli into the dermis. An embodiment delivers ultrasound energy to the region creating a thermal injury and coagulating the proximal protrusions of fat lobuli, thereby eliminating the fat protrusions into the dermis. An embodiment can also include ultrasound imaging configurations using the same or a separate probe before, after or during the treatment. In addition various therapeutic levels of ultrasound can be used to increase the speed at which fat metabolizes. Additionally the mechanical action of ultrasound physically breaks fat cell clusters and stretches the fibrous bonds. Mechanical action will also enhance lymphatic drainage, stimulating the evacuation of fat decay products.

20 Claims, 18 Drawing Sheets

Related U.S. Application Data continuation of application No. 15/041,829, filed on Feb. 11, 2016, now Pat. No. 9,522,290, which is a continuation of application No. 14/550,720, filed on Nov. 21, 2014, now Pat. No. 9,283,410, which is a continuation of application No. 14/164,598, filed on Jan. 27, 2014, now Pat. No. 8,915,854, which is a continuation of application No. 13/789,562, filed on Mar. 7, 2013, now Pat. No. 8,636,665, which is a continuation of application No. 13/356,405, filed on Jan. 23, 2012, now Pat. No. 8,672,848, which is a continuation of application No. 11/163,154, filed on Oct. 6, 2005, now Pat. No. 8,133,180.

(60) Provisional application No. 60/616,753, filed on Oct. 6, 2004.

(51) Int. Cl.
    *G01S 15/89*      (2006.01)
    *A61N 7/00*      (2006.01)
    *A61B 8/14*      (2006.01)
    *A61B 8/08*      (2006.01)
    *A61B 90/00*      (2016.01)

(52) U.S. Cl.
    CPC .............. *A61B 8/461* (2013.01); *A61B 8/483* (2013.01); *A61N 7/00* (2013.01); *G01S 15/8906* (2013.01); *G01S 15/8936* (2013.01); *A61B 8/4455* (2013.01); *A61B 2090/378* (2016.02); *A61N 2007/0008* (2013.01)

(58) Field of Classification Search
    CPC ....... A61B 8/4483; A61B 8/461; A61B 8/483; A61B 2090/378; G01S 15/8906; G01S 15/8936
    See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |

(56) References Cited

U.S. PATENT DOCUMENTS

| | | | |
|---|---|---|---|
| 5,255,681 A | 10/1993 | Ishimura et al. | |
| 5,257,970 A | 11/1993 | Dougherty | |
| 5,265,614 A | 11/1993 | Hayakawa | |
| 5,267,985 A | 12/1993 | Shimada | |
| 5,269,297 A | 12/1993 | Weng | |
| 5,282,797 A | 2/1994 | Chess | |
| 5,295,484 A | 3/1994 | Marcus | |
| 5,295,486 A | 3/1994 | Wollschlager et al. | |
| 5,304,169 A | 4/1994 | Sand | |
| 5,305,756 A | 4/1994 | Entrekin et al. | |
| 5,321,520 A | 6/1994 | Inga et al. | |
| 5,323,779 A | 6/1994 | Hardy et al. | |
| 5,327,895 A | 7/1994 | Hashimoto et al. | |
| 5,348,016 A | 9/1994 | Unger et al. | |
| 5,358,466 A * | 10/1994 | Aida | A61B 17/2256 600/439 |
| 5,360,268 A | 11/1994 | Hayashi | |
| 5,370,121 A | 12/1994 | Reichenberger | |
| 5,370,122 A | 12/1994 | Kunig et al. | |
| 5,371,483 A | 12/1994 | Bhardwaj | |
| 5,375,602 A | 12/1994 | Lancee et al. | |
| 5,379,773 A | 1/1995 | Hornsby | |
| 5,380,280 A | 1/1995 | Peterson | |
| 5,380,519 A | 1/1995 | Schneider et al. | |
| 5,383,917 A | 1/1995 | Desai et al. | |
| 5,391,140 A | 2/1995 | Schaetzle et al. | |
| 5,391,197 A | 2/1995 | Burdette et al. | |
| 5,392,259 A | 2/1995 | Bolorforosh | |
| 5,396,143 A | 3/1995 | Seyed-Bolorforosh et al. | |
| 5,398,689 A | 3/1995 | Connor et al. | |
| 5,406,503 A | 4/1995 | Williams | |
| 5,413,550 A * | 5/1995 | Castel | A61H 23/0245 601/2 |
| 5,417,216 A | 5/1995 | Tanaka | |
| 5,419,327 A | 5/1995 | Rohwedder | |
| 5,423,220 A | 6/1995 | Finsterwald et al. | |
| 5,435,311 A | 7/1995 | Umemura | |
| 5,438,998 A | 8/1995 | Hanafy | |
| 5,443,068 A * | 8/1995 | Cline | A61B 5/0555 600/411 |
| 5,445,611 A | 8/1995 | Eppstein et al. | |
| 5,458,596 A | 10/1995 | Lax | |
| 5,460,179 A | 10/1995 | Okunuki et al. | |
| 5,460,595 A | 10/1995 | Hall et al. | |
| 5,469,854 A | 11/1995 | Unger et al. | |
| 5,471,488 A | 12/1995 | Fujio | |
| 5,472,405 A | 12/1995 | Buchholtz et al. | |
| 5,487,388 A | 1/1996 | Rello et al. | |
| 5,492,126 A | 2/1996 | Hennige | |
| 5,496,256 A | 3/1996 | Bock | |
| 5,501,655 A | 3/1996 | Rolt | |
| 5,503,152 A | 4/1996 | Oakley et al. | |
| 5,503,320 A | 4/1996 | Webster et al. | |
| 5,507,790 A | 4/1996 | Weiss | |
| 5,511,296 A | 4/1996 | Dias et al. | |
| 5,520,188 A | 5/1996 | Hennige | |
| 5,522,869 A | 6/1996 | Burdette | |
| 5,523,058 A | 6/1996 | Umemura et al. | |
| 5,524,620 A | 6/1996 | Rosenchein | |
| 5,524,624 A | 6/1996 | Tepper | |
| 5,524,625 A | 6/1996 | Okazaki | |
| 5,526,624 A | 6/1996 | Berg | |
| 5,526,812 A | 6/1996 | Dumoulin et al. | |
| 5,526,814 A | 6/1996 | Cline et al. | |
| 5,526,815 A | 6/1996 | Granz | |
| 5,529,070 A | 6/1996 | Augustine et al. | |
| 5,540,235 A | 7/1996 | Wilson | |
| 5,558,092 A | 9/1996 | Unger | |
| 5,560,362 A | 10/1996 | Sliwa et al. | |
| 5,575,291 A | 11/1996 | Hayakawa | |
| 5,575,807 A | 11/1996 | Faller | |
| 5,577,502 A | 11/1996 | Darrow et al. | |
| 5,577,507 A | 11/1996 | Snyder et al. | |
| 5,577,991 A | 11/1996 | Akui et al. | |
| 5,580,575 A | 12/1996 | Unger et al. | |
| 5,601,526 A * | 2/1997 | Chapelon | A61N 7/02 601/2 |
| 5,603,323 A | 2/1997 | Pflugrath et al. | |
| 5,605,154 A * | 2/1997 | Ries | G01S 7/52046 600/444 |
| 5,609,562 A | 3/1997 | Kaali | |
| 5,615,091 A | 3/1997 | Palatnik | |
| 5,618,275 A | 4/1997 | Bock | |
| 5,620,479 A | 4/1997 | Diederich | |
| 5,622,175 A | 4/1997 | Sudol et al. | |
| 5,617,858 A | 5/1997 | Taverna et al. | |
| 5,638,819 A | 6/1997 | Manwaring et al. | |
| 5,643,179 A * | 7/1997 | Fujimoto | A61N 7/02 601/2 |
| 5,644,085 A | 7/1997 | Lorraine et al. | |
| 5,647,373 A | 7/1997 | Paltieli | |
| 5,655,535 A | 8/1997 | Friemel et al. | |
| 5,655,538 A | 8/1997 | Lorraine | |
| 5,657,760 A | 8/1997 | Ying | |
| 5,658,328 A | 8/1997 | Johnson | |
| 5,660,836 A * | 8/1997 | Knowlton | A61B 18/12 128/898 |
| 5,662,116 A | 9/1997 | Kondo | |
| 5,665,053 A | 9/1997 | Jacobs | |
| 5,665,141 A | 9/1997 | Vago | |
| 5,671,746 A | 9/1997 | Dreschel et al. | |
| 5,673,699 A | 10/1997 | Trahey et al. | |
| 5,676,692 A | 10/1997 | Sanghvi | |
| 5,685,820 A | 11/1997 | Riek et al. | |
| 5,690,608 A | 11/1997 | Watanabe | |
| 5,694,936 A | 12/1997 | Fujimoto | |
| 5,697,897 A | 12/1997 | Buchholtz | |
| 5,701,900 A | 12/1997 | Shehada et al. | |
| 5,704,361 A | 1/1998 | Seward et al. | |
| 5,706,252 A | 1/1998 | Le Verrier et al. | |
| 5,706,564 A | 1/1998 | Rhyne | |
| 5,715,823 A | 2/1998 | Wood et al. | |
| 5,720,287 A | 2/1998 | Chapelon et al. | |
| 5,722,411 A | 3/1998 | Suzuki | |
| 5,727,554 A | 3/1998 | Kalend et al. | |
| 5,735,280 A | 4/1998 | Sherman et al. | |
| 5,743,863 A | 4/1998 | Chapelon | |
| 5,746,005 A | 5/1998 | Steinberg | |
| 5,746,762 A | 5/1998 | Bass | |
| 5,748,767 A | 5/1998 | Raab | |
| 5,749,364 A | 5/1998 | Sliwa et al. | |
| 5,755,228 A | 5/1998 | Wilson et al. | |
| 5,755,753 A | 5/1998 | Knowlton | |
| 5,762,066 A | 6/1998 | Law | |
| 5,763,886 A | 6/1998 | Schulte | |
| 5,769,790 A | 6/1998 | Watkins | |
| 5,779,644 A | 7/1998 | Eberle et al. | |
| 5,792,058 A | 8/1998 | Lee | |
| 5,795,297 A | 8/1998 | Daigle | |
| 5,795,311 A | 8/1998 | Wess | |
| 5,810,009 A | 9/1998 | Mine et al. | |
| 5,810,888 A | 9/1998 | Fenn | |
| 5,814,599 A | 9/1998 | Mitragotri et al. | |
| 5,817,013 A | 10/1998 | Ginn et al. | |
| 5,817,021 A | 10/1998 | Reichenberger | |
| 5,820,564 A | 10/1998 | Slayton | |
| 5,823,962 A | 10/1998 | Schaetzle | |
| 5,827,204 A | 10/1998 | Grandia et al. | |
| 5,840,032 A | 11/1998 | Hatfield et al. | |
| 5,844,140 A | 12/1998 | Seale | |
| 5,853,367 A | 12/1998 | Chalek et al. | |
| 5,869,751 A | 2/1999 | Bonin | |
| 5,871,524 A | 2/1999 | Knowlton | |
| 5,873,902 A | 2/1999 | Sanghvi | |
| 5,876,341 A | 3/1999 | Wang et al. | |
| 5,879,303 A | 3/1999 | Averkiou et al. | |
| 5,882,557 A | 3/1999 | Hayakawa | |
| 5,891,034 A | 4/1999 | Bucholz | |
| 5,895,356 A | 4/1999 | Andrus et al. | |
| 5,899,861 A | 5/1999 | Friemel et al. | |
| 5,904,659 A | 5/1999 | Duarte | |
| 5,919,219 A | 7/1999 | Knowlton | |
| 5,923,099 A | 7/1999 | Bilir | |
| 5,924,989 A | 7/1999 | Polz | |

(56) References Cited

U.S. PATENT DOCUMENTS

| | | | |
|---|---|---|---|
| 5,928,169 A | 7/1999 | Schatzle et al. | |
| 5,931,805 A | 8/1999 | Brisken | |
| 5,938,606 A | 8/1999 | Bonnefous | |
| 5,938,612 A | 8/1999 | Kline-Schoder | |
| 5,948,011 A | 9/1999 | Knowlton | |
| 5,957,844 A | 9/1999 | Dekel | |
| 5,957,882 A | 9/1999 | Nita et al. | |
| 5,957,941 A | 9/1999 | Ream | |
| 5,964,707 A | 10/1999 | Fenster et al. | |
| 5,967,980 A | 10/1999 | Ferre et al. | |
| 5,968,034 A | 10/1999 | Fullmer | |
| 5,971,949 A | 10/1999 | Levin | |
| 5,977,538 A | 11/1999 | Unger et al. | |
| 5,984,881 A * | 11/1999 | Ishibashi | A61B 17/2256 601/2 |
| 5,984,882 A | 11/1999 | Rosenchein | |
| 5,990,598 A | 11/1999 | Sudol et al. | |
| 5,997,471 A | 12/1999 | Gumb et al. | |
| 5,997,497 A | 12/1999 | Nita et al. | |
| 5,999,843 A | 12/1999 | Anbar | |
| 6,004,262 A | 12/1999 | Putz et al. | |
| 6,007,499 A | 12/1999 | Martin et al. | |
| 6,013,032 A | 1/2000 | Savord | |
| 6,014,473 A | 1/2000 | Hossack et al. | |
| 6,016,255 A | 1/2000 | Bolan et al. | |
| 6,019,724 A | 2/2000 | Gronningsaeter et al. | |
| 6,022,308 A | 2/2000 | Williams | |
| 6,022,327 A | 2/2000 | Chang | |
| 6,030,374 A | 2/2000 | McDaniel | |
| 6,036,646 A | 3/2000 | Barthe | |
| 6,039,048 A | 3/2000 | Silberg | |
| 6,039,689 A | 3/2000 | Lizzi | |
| 6,042,556 A * | 3/2000 | Beach | A61N 7/02 600/437 |
| 6,049,159 A | 4/2000 | Barthe | |
| 6,050,943 A | 4/2000 | Slayton | |
| 6,059,727 A | 5/2000 | Fowlkes | |
| 6,071,239 A | 6/2000 | Cribbs | |
| 6,080,108 A | 6/2000 | Dunham | |
| 6,083,148 A | 7/2000 | Williams | |
| 6,086,535 A | 7/2000 | Ishibashi | |
| 6,086,580 A | 7/2000 | Mordon et al. | |
| 6,090,054 A | 7/2000 | Tagishi | |
| 6,093,148 A * | 7/2000 | Fujimoto | A61N 7/00 600/438 |
| 6,093,883 A | 7/2000 | Sanghvi | |
| 6,101,407 A | 8/2000 | Groezinger | |
| 6,106,469 A | 8/2000 | Suzuki et al. | |
| 6,113,558 A | 9/2000 | Rosenchein | |
| 6,113,559 A | 9/2000 | Klopotek | |
| 6,120,452 A | 9/2000 | Barthe | |
| 6,123,081 A | 9/2000 | Durette | |
| 6,126,619 A | 10/2000 | Peterson et al. | |
| 6,135,971 A | 10/2000 | Hutchinson | |
| 6,139,499 A | 10/2000 | Wilk | |
| 6,159,150 A | 12/2000 | Yale et al. | |
| 6,171,244 B1 | 1/2001 | Finger et al. | |
| 6,176,840 B1 | 1/2001 | Nishimura | |
| 6,183,426 B1 | 2/2001 | Akisada | |
| 6,183,502 B1 | 2/2001 | Takeuchi | |
| 6,183,773 B1 | 2/2001 | Anderson | |
| 6,190,323 B1 | 2/2001 | Dias | |
| 6,190,336 B1 | 2/2001 | Duarte | |
| 6,193,658 B1 | 2/2001 | Wendelken | |
| 6,210,327 B1 | 4/2001 | Brackett et al. | |
| 6,213,948 B1 | 4/2001 | Barthe | |
| 6,216,029 B1 | 4/2001 | Paltieli | |
| 6,233,476 B1 | 5/2001 | Strommer et al. | |
| 6,234,990 B1 | 5/2001 | Rowe et al. | |
| 6,241,753 B1 * | 6/2001 | Knowlton | A61B 18/12 128/898 |
| 6,246,898 B1 | 6/2001 | Vesely et al. | |
| 6,251,074 B1 | 6/2001 | Averkiou et al. | |
| 6,251,088 B1 | 6/2001 | Kaufman et al. | |
| 6,268,405 B1 | 7/2001 | Yao | |
| 6,273,864 B1 | 8/2001 | Duarte | |
| 6,280,402 B1 | 8/2001 | Ishibashi et al. | |
| 6,287,257 B1 | 9/2001 | Matichuk | |
| 6,287,304 B1 | 9/2001 | Eggers et al. | |
| 6,296,619 B1 | 10/2001 | Brisken | |
| 6,301,989 B1 | 10/2001 | Brown et al. | |
| 6,307,302 B1 | 10/2001 | Toda | |
| 6,309,355 B1 | 10/2001 | Cain et al. | |
| 6,311,090 B1 | 10/2001 | Knowlton | |
| 6,315,741 B1 * | 11/2001 | Martin | A61B 8/4254 601/3 |
| 6,322,509 B1 | 11/2001 | Pan et al. | |
| 6,322,532 B1 | 11/2001 | D'Sa | |
| 6,325,540 B1 | 12/2001 | Lounsberry et al. | |
| 6,325,758 B1 | 12/2001 | Carol et al. | |
| 6,325,769 B1 | 12/2001 | Klopotek | |
| 6,325,798 B1 | 12/2001 | Edwards et al. | |
| 6,350,276 B1 | 2/2002 | Knowlton | |
| 6,356,780 B1 | 3/2002 | Licato et al. | |
| 6,361,531 B1 | 3/2002 | Hissong | |
| 6,370,411 B1 | 4/2002 | Osadchy et al. | |
| 6,375,672 B1 | 4/2002 | Aksan | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,390,982 B1 | 5/2002 | Bova et al. | |
| 6,405,090 B1 | 6/2002 | Knowlton | |
| 6,409,720 B1 | 6/2002 | Hissong | |
| 6,413,216 B1 | 7/2002 | Cain et al. | |
| 6,413,253 B1 | 7/2002 | Koop | |
| 6,413,254 B1 | 7/2002 | Hissong | |
| 6,419,648 B1 | 7/2002 | Vitek | |
| 6,423,007 B2 | 7/2002 | Lizzi et al. | |
| 6,425,865 B1 | 7/2002 | Salcudean | |
| 6,425,867 B1 | 7/2002 | Vaezy | |
| 6,425,912 B1 | 7/2002 | Knowlton | |
| 6,428,477 B1 | 8/2002 | Mason | |
| 6,428,532 B1 | 8/2002 | Doukas | |
| 6,430,446 B1 | 8/2002 | Knowlton | |
| 6,432,057 B1 | 8/2002 | Mazess et al. | |
| 6,432,067 B1 | 8/2002 | Martin | |
| 6,432,101 B1 | 8/2002 | Weber | |
| 6,436,061 B1 | 8/2002 | Costantino | |
| 6,438,424 B1 | 8/2002 | Knowlton | |
| 6,440,071 B1 | 8/2002 | Slayton | |
| 6,440,121 B1 | 8/2002 | Weber | |
| 6,443,914 B1 | 9/2002 | Costantino | |
| 6,447,443 B1 | 9/2002 | Keogh et al. | |
| 6,451,013 B1 | 9/2002 | Bays et al. | |
| 6,453,202 B1 | 9/2002 | Knowlton | |
| 6,461,304 B1 | 10/2002 | Tanaka et al. | |
| 6,461,378 B1 | 10/2002 | Knowlton | |
| 6,470,216 B1 | 10/2002 | Knowlton | |
| 6,338,716 B1 | 11/2002 | Hossack et al. | |
| 6,488,626 B1 | 12/2002 | Lizzi | |
| 6,491,657 B2 | 12/2002 | Rowe | |
| 6,500,121 B1 | 12/2002 | Slayton | |
| 6,500,141 B1 | 12/2002 | Irion | |
| 6,506,171 B1 | 1/2003 | Vitek et al. | |
| 6,508,774 B1 | 1/2003 | Acker | |
| 6,511,427 B1 | 1/2003 | Sliwa, Jr. et al. | |
| 6,511,428 B1 | 1/2003 | Azuma | |
| 6,514,244 B2 | 2/2003 | Pope | |
| 6,517,484 B1 | 2/2003 | Wilk | |
| 6,524,250 B1 | 2/2003 | Weber | |
| 6,666,835 B2 | 3/2003 | Martin | |
| 6,540,679 B2 | 4/2003 | Slayton | |
| 6,540,685 B1 | 4/2003 | Rhoads et al. | |
| 6,540,700 B1 | 4/2003 | Fujimoto et al. | |
| 6,547,788 B1 | 4/2003 | Maguire et al. | |
| 6,554,771 B1 | 4/2003 | Buil et al. | |
| 6,569,099 B1 | 5/2003 | Babaev | |
| 6,569,108 B2 | 5/2003 | Sarvazyan et al. | |
| 6,572,552 B2 | 6/2003 | Fukukita | |
| 6,575,956 B1 | 6/2003 | Brisken et al. | |
| 6,595,934 B1 | 7/2003 | Hissong | |
| 6,599,256 B1 | 7/2003 | Acker | |

(56) References Cited

U.S. PATENT DOCUMENTS

| | | | |
|---|---|---|---|
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,631,611 B1 | 12/2009 | Dick et al. |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |

(56) References Cited

U.S. PATENT DOCUMENTS

| | | |
|---|---|---|
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,640,193 B2 | 1/2014 | Shigeeda |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,095,697 B2 | 8/2015 | Barthe et al. |
| 9,114,247 B2 | 8/2015 | Barthe et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,320,537 B2 | 4/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,440,096 B2 | 9/2016 | Barthe et al. |
| 9,510,802 B2 | 12/2016 | Barthe et al. |
| 9,522,290 B2 | 12/2016 | Slayton et al. |
| 9,533,175 B2 | 1/2017 | Slayton et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1* | 10/2001 | Weng ............... A61B 17/0057 600/439 |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1* | 1/2003 | McDaniel ............... A61K 8/02 607/88 |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |

(56) References Cited

U.S. PATENT DOCUMENTS

| | | |
|---|---|---|
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |

(56) References Cited

U.S. PATENT DOCUMENTS

| | | |
|---|---|---|
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0066084 A1 | 3/2011 | Desilets et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2015/0000674 A1 | 1/2015 | Barthe et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0027994 A1 | 1/2016 | Toda et al. |
| 2016/0175619 A1 | 6/2016 | Lee et al. |
| 2016/0206335 A1 | 7/2016 | Slayton |

(56) References Cited

U.S. PATENT DOCUMENTS

| | | |
|---|---|---|
| 2016/0206341 A1 | 7/2016 | Slayton |
| 2016/0256675 A1 | 9/2016 | Slayton |
| 2016/0296769 A1 | 10/2016 | Barthe et al. |

FOREIGN PATENT DOCUMENTS

| | | |
|---|---|---|
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 1283690 | 2/2003 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001170068 | 6/2001 |
| JP | 2002505596 | 2/2002 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004-509671 | 4/2004 |
| JP | 2004-512856 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9949788 | 10/1999 |
| WO | WO200006032 | 2/2000 |
| WO | WO0015300 | 3/2000 |
| WO | WO0021612 | 4/2000 |
| WO | WO0053113 | 9/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |
| WO | WO2001087161 | 11/2001 |
| WO | WO 02/09812 | 2/2002 |
| WO | WO0209813 | 2/2002 |
| WO | WO02015768 | 2/2002 |
| WO | WO0224050 | 3/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO2002054018 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2007067563 | 6/2007 |
| WO | WO2008036622 | 3/2008 |
| WO | WO2008036479 | 11/2008 |
| WO | WO2009013729 | 1/2009 |
| WO | WO2009149390 | 10/2009 |
| WO | WO2008144274 | 1/2010 |
| WO | WO2012134645 | 1/2013 |
| WO | WO2014045216 | 3/2014 |
| WO | WO2014055708 | 4/2014 |
| WO | WO2014057388 | 4/2014 |

OTHER PUBLICATIONS

U.S. Appl. No. 13/245,822, filed Sep. 26, 2011, System and Method for Cosmetic Treatment.

U.S. Appl. No. 13/245,852, filed Sep. 26, 2011, Systems for Cosmetic Treatment.

(56) References Cited

OTHER PUBLICATIONS

U.S. Appl. No. 13/245,864, filed Sep. 27, 2011, Methods for Non-Invasive Cosmetic Treatment of the Eye Region.
U.S. Appl. No. 13/246,117, filed Sep. 27, 2011, Methods for Non-Invasive Lifting and Tightening of the Lower Face and Neck.
U.S. Appl. No. 13/246,112, filed Sep. 27, 2011, Tissue Imaging and Treatment Method.
U.S. Appl. No. 14/193,234, filed Feb. 28, 2014, Devices and Methods for Multi-Focus Ultrasound Therapy.
U.S. Appl. No. 15/302,436, filed Oct. 6, 2016, Band Transducer Ultrasound Therapy.
U.S. Appl. No. 08/950,353, filed Oct. 14, 1997, Imaging, Therapy and Temperature Monitoring Ultrasonic System.
U.S. Appl. No. 09/502,174, filed Feb. 10, 2000, Imaging, Therapy and Temperature Monitoring Ultrasonic System.
U.S. Appl. No. 10/193,419, filed Jul. 10, 2002, Imaging, Therapy and Temperature Monitoring Ultrasonic System.
U.S. Appl. No. 10/944,499, filed Sep. 16, 2004, Method and System for Ultrasound Treatment With a Multi-Directional Transducer.
U.S. Appl. No. 11/163,177, filed Oct. 7, 2005, Method and System for Treating Acne and Sebaceous Glands.
U.S. Appl. No. 10/950,112, filed Sep. 24, 2004, Method and System for Combined Ultrasound Treatment.
U.S. Appl. No. 11/163,178, filed Oct. 7, 2005, Method and System for Treating Stretch Marks.
U.S. Appl. No. 11/245,999, filed Oct. 6, 2005, System and Method for Ultra-High Frequency Ultrasound Treatment.
U.S. Appl. No. 10/944,500, filed Sep. 16, 2004, System and Method for Variable Depth Ultrasound Treatment.
U.S. Appl. No. 11/744,655, filed May 4, 2007, Imaging, Therapy and Temperature Monitoring Ultrasonic System.
U.S. Appl. No. 13/937,190, filed Jul. 8, 2013, Imaging, Therapy and Temperature Monitoring Ultrasonic System.
U.S. Appl. No. 12/135,962, filed Jun. 9, 2008, Method and System for Ultrasound Treatment With a Multi-Directional Transducer.
U.S. Appl. No. 12/792,934, filed Jun. 3, 2010, System and Method for Ultra-High Frequency Ultrasound Treatment.
U.S. Appl. No. 13/914,945, filed Jun. 11, 2013, System and Method for Ultra-High Frequency Ultrasound Treatment.
U.S. Appl. No. 12/834,754, filed Jul. 12, 2010, System and Method for Variable Depth Ultrasound Treatment.
U.S. Appl. No. 14/264,732, filed Apr. 29, 2014, System and Method for Variable Depth Ultrasound Treatment.
U.S. Appl. No. 11/126,760, filed May 11, 2005, Method and System for Three-Dimensional Scanning and Imaging.
U.S. Appl. No. 13/564,552, filed Aug. 1, 2012, Method and System for Controlled Scanning, Imaging and/or Therapy.
U.S. Appl. No. 12/437,726, filed May 8, 2009, Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Customized Cosmetic Treatment.
U.S. Appl. No. 11/163,152, filed Oct. 6, 2005, Method and System for Treatment of Sweat Glands.
U.S. Appl. No. 13/444,485, filed Apr. 11, 2012, Methods for Treatment of Sweat Glands.
U.S. Appl. No. 13/603,159, filed Sep. 4, 2012, Methods for Treatment of Hyperhidrosis.
U.S. Appl. No. 13/603,279, filed Sep. 4, 2012, Energy Based Hyperhidrosis Treatment.
U.S. Appl. No. 13/950,728, filed Jul. 25, 2013, Energy Based Hyperhidrosis Treatment.
U.S. Appl. No. 14/571,835, filed Dec. 16, 2014, Energy Based Hyperhidrosis Treatment.
U.S. Appl. No. 15/243,081, filed Aug. 22, 2016, Energy Based Hyperhidrosis Treatment.
U.S. Appl. No. 11/163,151, filed Oct. 6, 2005, Method and System for Noninvasive Face Lifts and Deep Tissue Tightening.
U.S. Appl. No. 13/444,336, filed Apr. 11, 2012, Treatment of Sub-Dermal Regions for Cosmetic Effects.
U.S. Appl. No. 13/679,430, filed Nov. 16, 2012, Ultrasound Treatment of Sub-Dermal Tissue for Cosmetic Effects.
U.S. Appl. No. 13/924,376, filed Jun. 21, 2013, Noninvasive Tissue Tightening for Cosmetic Effects.
U.S. Appl. No. 13/924,355, filed Jun. 21, 2013, Noninvasive Aesthetic Treatment for Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 12/028,636, filed Feb. 8, 2008, Method and System for Noninvasive Face Lifts and Deep Tissue Tightening.
U.S. Appl. No. 13/964,820, filed Aug. 12, 2013, Methods for Noninvasive Skin Tightening.
U.S. Appl. No. 14/201,256, filed Mar. 7, 2014, System for Noninvasive Skin Tightening.
U.S. Appl. No. 15/098,139, filed Apr. 13, 2016, System and Method for Noninvasive Skin Tightening.
U.S. Appl. No. 14/685,390, filed Apr. 13, 2015, Energy-Based Tissue Tightening System.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 14/169,709, filed Jan. 31, 2014, Methods for Treating Skin Laxity.
U.S. Appl. No. 14/692,114, filed Apr. 21, 2015, Systems for Treating Skin Laxity.
U.S. Appl. No. 15/248,407, filed Aug. 26, 2016, Systems for Treating Skin Laxity.
U.S. Appl. No. 11/163,176, filed Oct. 7, 2005, Method and System for Treating Blood Vessel Disorders.
U.S. Appl. No. 13/601,742, filed Aug. 31, 2012, Method and System for Treating Blood Vessel Disorders.
U.S. Appl. No. 12/574,512, filed Oct. 6, 2009, Method and System for Treating Stretch Marks.
U.S. Appl. No. 14/554,668, filed Nov. 26, 2014, Method and System for Treating Stretch Marks.
U.S. Appl. No. 15/260,825, filed Sep. 12, 2016, Method and System for Treating Stretch Marks.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 13/835,635, filed Mar. 15, 2013, Methods for Face and Neck Lifts.
U.S. Appl. No. 13/965,741, filed Aug. 13, 2013, Methods for Preheating Tissue for Cosmetic Treatment of the Face and Body.
U.S. Appl. No. 14/740,092, filed Jun. 15, 2015, Methods for Rejuvenating Skin by Heating Tissue for Cosmetic Treatment of the Face and Body.
U.S. Appl. No. 14/628,198, filed Feb. 20, 2015, System and Method for Treating Cartilage and Injuries to Joints and Connective Tissue.
U.S. Appl. No. 14/554,571, filed Nov. 26, 2014, Methods for Face and Neck Lifts.
U.S. Appl. No. 15/248,454, filed Aug. 26, 2016, Methods for Face and Neck Lifts.
U.S. Appl. No. 12/954,484, filed Nov. 24, 2010, Methods and Systems for Generating Thermal Bubbles for Improved Ultrasound Imaging and Therapy.
U.S. Appl. No. 12/350,383, filed Jan. 8, 2009, Method and System for Treating Acne and Sebaceous Glands.
U.S. Appl. No. 12/116,845, filed May 7, 2008, Method and System for Combined Energy Profile.
U.S. Appl. No. 14/643,749, filed Mar. 10, 2015, Method and System for Combined Energy Profile.
U.S. Appl. No. 08/766,083, filed Dec. 16, 1996, Method and Apparatus for Surface Ultrasound Imaging.

(56) References Cited

OTHER PUBLICATIONS

U.S. Appl. No. 09/113,227, filed Jul. 10, 1998, Method and Apparatus for Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method and Apparatus for Three Dimensional Ultrasound Imaging.
U.S. Appl. No. 09/523,890, filed Mar. 13, 2000, Method and Apparatus for Three Dimensional Ultrasound Imaging.
U.S. Appl. No. 09/419,543, filed Oct. 18, 1999, Peripheral Ultrasound Imaging System.
U.S. Appl. No. 09/750,816, filed Dec. 28, 2000, Visual Imaging System for Ultrasonic Probe.
U.S. Appl. No. 10/358,110, filed Feb. 4, 2003, Visual Imaging System for Ultrasonic Probe.
U.S. Appl. No. 11/380,161, filed Apr. 25, 2006, Method and System for Enhancing Computer Peripheral Safety.
U.S. Appl. No. 11/554,272, filed Oct. 30, 2006, Visual Imaging System for Ultrasonic Probe.
U.S. Appl. No. 13/071,298, filed Mar. 24, 2011, Visual Imaging System for Ultrasonic Probe.
U.S. Appl. No. 13/854,936, filed Mar. 25, 2013, Visual Imaging System for Ultrasonic Probe.
U.S. Appl. No. 12/509,254, filed Jul. 24, 2009, Method and System for Enhancing Computer Peripheral Safety.
U.S. Appl. No. 13/453,847, filed Apr. 23, 2012, Method and System for Enhancing Computer Peripheral Safety.
U.S. Appl. No. 11/538,794, filed Oct. 4, 2006, Ultrasound System and Method for Imaging and/or Measuring Displacement of Moving Tissue and Fluid.
U.S. Appl. No. 09/502,175, filed Feb. 10, 2000, Method and Apparatus for Safely Delivering Medicants to a Region of Tissue, Using Imaging, Therapy and Temperature Monitoring.
U.S. Appl. No. 08/943,728, filed Oct. 3, 1997, Method and Apparatus for Safely Delivering Medicants to a Region of Tissue Using Ultrasound.
U.S. Appl. No. 12/415,945, filed Mar. 31, 2009, Method and System for Noninvasive Mastopexy.
U.S. Appl. No. 11/163,155, filed Oct. 6, 2005, Method and System for Noninvasive Mastopexy.
U.S. Appl. No. 11/163,154, filed Oct. 6, 2005, Method and System for Treatment of Cellulite.
U.S. Appl. No. 13/356,405, filed Jan. 23, 2012, Method and System for Treatment of Cellulite.
U.S. Appl. No. 13/789,562, filed Mar. 7, 2013, Method and System for Ultrasound Treatment of Fat.
U.S. Appl. No. 14/164,598, filed Jan. 27, 2013, Method for Fat and Cellulite Reduction.
U.S. Appl. No. 14/550,720, filed Nov. 21, 2014, System and Method for Fat and Cellulite Reduction.
U.S. Appl. No. 15/041,829, filed Feb. 11, 2016, System and Method for Fat and Cellulite Reduction.
U.S. Appl. No. 15/374,918, filed Dec. 9, 2016, System and Method for Fat and Cellulite Reduction.
U.S. Appl. No. 11/738,682, filed Apr. 23, 2007, Method and System for Non-Ablative Acne Treatment and Prevention.
U.S. Appl. No. 12/116,810, filed May 7, 2008, Methods and Systems for Modulating Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/646,609, filed Dec. 23, 2009, Methods and System for Fat Reduction and/or Cellulite Treatment.
U.S. Appl. No. 14/192,520, filed Feb. 27, 2014, Energy Based Fat Reduction.
U.S. Appl. No. 14/550,772, filed Nov. 21, 2014, Energy Based Fat Reduction.
U.S. Appl. No. 15/401,804, filed Feb. 11, 2016, Energy Based Fat Reduction.
U.S. Appl. No. 15/380,267, filed Dec. 15, 2016, Energy Based Fat Reduction.
U.S. Appl. No. 13/291,312, filed Nov. 11, 2011, Devices and Methods for Acoustic Shielding.
U.S. Appl. No. 14/487,504, filed Sep. 16, 2014, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into a Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems and Methods for Improving an Outside Appearance of Skin Using Ultrasound as an Energy Source.
U.S. Appl. No. 13/545,945, filed Jul. 10, 2012, Systems and Methods for Treating Injuries to Joints and Connective Tissue.
U.S. Appl. No. 13/545,929, filed Jul. 10, 2012, Methods and Systems for Ultrasound Treatment.
U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/847,626, filed Sep. 8, 2015, Systems for Cosmetic Treatment.
U.S. Appl. No. 13/863,362, filed Apr. 15, 2013, Thick Film Transducer Arrays.
U.S. Appl. No. 14/217,110, filed Mar. 17, 2014, Ultrasound Treatment Device and Method of Use.
U.S. Appl. No. 14/217,382, filed Mar. 17, 2014, Ultrasound Treatment Device and Method of Use.
U.S. Appl. No. 14/225,189, filed Mar. 25, 2014, Reflective Ultrasound Technology for Dermatological Treatments.
U.S. Appl. No. 15/345,908, filed Nov. 8, 2016, Reflective Ultrasound Technology for Dermatological Treatments.
U.S. Appl. No. 14/270,859, filed May 6, 2014, Methods and Systems for Generating Thermal Bubbles for Improved Ultrasound Imaging and Therapy.
U.S. Appl. No. 14/679,494, filed Apr. 6, 2015, Methods and Systems for Generating Thermal Bubbles for Improved Ultrasound Imaging and Therapy.
U.S. Appl. No. 14/405,368, filed Dec. 3, 2014, Devices and Methods for Ultrasound Focal Depth Control.
U.S. Appl. No. 14/568,954, filed Dec. 12, 2014, System and Method for Cosmetic Enhancement of Lips.
U.S. Appl. No. 14/569,001, filed Dec. 12, 2014, System and Method for Non-Invasive Treatment With Improved Efficiency.
U.S. Appl. No. 14/600,782, filed Jan. 20, 2015, Methods and Systems for Controlling and Acoustic Energy Deposition in Various Media.
U.S. Appl. No. 14/738,420, filed Jun. 12, 2015, Systems and Methods for Fast Ultrasound Treatment.
U.S. Appl. No. 14/751,349, filed Jun. 26, 2015, Methods and Systems for Tattoo Removal.
U.S. Appl. No. 15/001,712, filed Jan. 20, 2016, Methods and Systems for Removal of a Targeted Tissue from a Body.
U.S. Appl. No. 15/001,621, filed Jan. 20, 2016, Methods and Systems for Removal of a Foreign Object from Tissue.

(56) References Cited

OTHER PUBLICATIONS

U.S. Appl. No. 15/059,773, filed Mar. 3, 2016, Methods and Systems for Material Transport Across an Impermeable or Semi-Permeable Membrane via Artificially Created Microchannels.
U.S. Appl. No. 15/094,774, filed Apr. 8, 2016, System and Method for Increased Control of Ultrasound Treatments.
Delon Martin, C., et al, "Venous Thrombosis Generation by Means of High-Intensity Focused Ultrasound" Ultrasound in Med. & Biol., vol. 21, No. 1, pp. 113-119 (1995).
Decision on Institution of Inter Partes Review in Re U.S. Pat. No. 6,113,559; IPR2016-01459; 20 pages [011] (Dated Jan. 23, 2017).
Dermafocus Response to Institution of Inter Partes Review in Re U.S. Pat. No. 6,113,559; IPR2016-01459; 73 pages [018] (Dated Apr. 26, 2017).
Dermafocus Exhibit List in Re U.S. Pat. No. 6,113,559; IPR2016-01459; 5 pages[019] (Dated Apr. 26, 2017).
Dermafocus Exhibit 2002, Declaration of Mark Palmeri, in Re U.S. Pat. No. 6,113,559; IPR2016-01459; 136 pages (Filed Apr. 26, 2017).
Dermafocus Exhibit 2003, Deposition of Dr. Mark Schafer, in Re U.S. Pat. No. 6,113,559; IPR2016-01459; 327 pages (Filed Apr. 26, 2017).
Dermafocus Exhibit 2004, Amendment No. 4 to Ulthera Form S-1, in Re U.S. Pat. No. 6,113,559; IPR2016-01459; 308 pages (Filed Apr. 26, 2017).
Dermafocus Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).
Dermafocus Exhibit 2006, Bo Eklof et al., "Revision of the CEAP Classification for Chronic Venous Disorders: Consensus Statement," Acta Fac Med Naiss, vol. 25, No. 1 (2008), 3-10 in Re U.S. Pat. No. 6,113,559; IPR2016-01459; 7 pages (Filed Apr. 26, 2017).
Dermafocus Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (Filed Apr. 26, 2017).
Dermafocus Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).
Dermafocus Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).
Dermafocus Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).
Dermafocus Exhibit 2011, U.S. Pat. No. 5,143,063, issued on Sep. 1,1992, Fellner, in Re U.S. Pat. No. 6,113,559; IPR2016-01459; 6 pages (Filed Apr. 26, 2017).
Dermafocus Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).
Dermafocus Exhibit 2013, Excerpt from Mosby's Medical Dictionary (3rd ed. 1990), in Re U.S. Pat. No. 6,113,559; IPR2016-01459; 4 pages (Filed Apr. 26, 2017).
Dermafocus Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).
Dermafocus Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).
Dermafocus Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (Filed Apr. 26, 2017).
Dermafocus Exhibit 2017, Email from Anderson to Klopotek dated May 25, 2004, in Re U.S. Pat. No. 6,113,559; IPR2016-01459; 1 page (Filed Apr. 26, 2017).
Dermafocus Exhibit 2018, List of Klopotek Patents, in Re U.S. Pat. No. 6,113,559; IPR2016-01459; 411 pages (Filed Apr. 26, 2017).
Dermafocus Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
Dermafocus Exhibit 2020, "Our Technology," http://jobs.ulthera.com/about on Apr. 10, downloaded from 2017, in Re U.S. Pat. No. 6,113,559; IPR2016-01459; 4 pages (Filed Apr. 26, 2017).
Dermafocus Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (Filed Apr. 26, 2017).
Dermafocus Exhibit 2022, Excerpt from Mosby's Medical Dictionary (5th ed. 1997), in Re U.S. Pat. No. 6,113,559; IPR2016-01459; 5 pages (Filed Apr. 26, 2017).
Dermafocus Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
Dermafocus Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).
Dermafocus Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
Dermafocus Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
Ulthera Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug 2, 2017 in re IPR2016-01459).
Ulthera Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug 2, 2017 in re IPR2016-01459).
Ulthera Exhibit 1024, Deposition Transcript of Dr. Mark Palmeri on Jul. 11, 2017 (filed Aug 2, 2017 in re IPR2016-01459).
Agren, Magnus S. et al., Collagenase in Wound Healing: Effect of Wound Age and Type. The Journal of Investigative Dermatology, vol. 99/No. 6, (Dec. 1992).
Alam, M., "The future of noninvasive procedural dermatology". Semin Cutan Med Surg. Mar. 2013; 32(1):59-61.
Alam, M., et al., "Ultrasound tightening of facial and neck skin: a rater-blinded prospective cohort study". J Am Acad Dermatol, 2010. 62(2): p. 262-9.
Alexiades-Armenakas, M., "Ultrasound Technologies for Dermatologic Techniques". J Drugs Derm. 2014. 12 (11): p. 1305.
Alster, T.S., et. al., "Noninvasive lifting of arm, thigh, and knee skin with transcutaneousintense focused ultrasound". Dermatol Surg, 2012. 38(5): p. 754-9.
Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Arosarena, O., "Options and Challenges for Facial Rejuvenation in Patients With Higher Fitzpatrick Skin Phototypes". JAMA Facial Plastic Surgery, 2015.

(56) References Cited

OTHER PUBLICATIONS

Arthur et al., "Non-invasive estimation of hyperthermia temperatures with ultrasound," Int. J. Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Bozec, Laurent et al., Thermal Denaturation Studies of Collagen by Microthermal Analysis and Atomic Force Microscopy, Biophysical Journal, vol. 101, pp. 228-236. (Jul. 2001).
Brobst, R.W., et. al., "Noninvasive Treatment of the Neck". Facial Plast Surg Clin North Am, 2014. 22(2): p. 191-202.
Brobst, R.W., et., al., "Ulthera: initial and six month results". Facial Plast Surg Clin North Am, 2012. 20(2): p. 163-76.
Calderhead et al., "One Mechanism Behind LED Photo-Therapy for Wound Healing and Skin Rejuvenation: Key Role of the Mast Cell" Laser Therapy 17.3: 141-148 (2008).
Casabona, G., et. al., "Microfocused Ultrasound With Visualization and Fillers for Increased Neocollagenesis: Clinical and Histological Evaluation". Dermatol Surg 2014;40:S194-S198.
Chan, N.P., et al., "Safety study of transcutaneous focused ultrasound for non-invasive skin tightening in Asians". Lasers Surg Med, 2011. 43(5): p. 366-75.
Chapelon et al., "Effects of Cavitation in the High Intensity Therapeutic Ultrasound", Ultrasonics Symposium—1357 (1991).
Chapelon, et al., "Thresholds for Tissue Ablation by Focused Ultrasound" (1990).
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., "Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).

Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fry, W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R. et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-l-Lactic Acid on the Face, Neck, and Décolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hitchcock, T.M. et. al., "Review of the safety profile for microfocused ultrasound with Visualization". Journal of Cosmetic Dermatology, 13, 329-335. (2014).
Husseini et al, "The Role of Cavitation in Acoustically Activated Drug Delivery," J. Control Release, Oct. 3, 2005, pp. 253-261, vol. 107(2).

(56) References Cited

OTHER PUBLICATIONS

Husseini et al. "Investigating the mechanism of acoustically activated uptake of drugs from Pluronic micelles," BMD Cancer 2002, 2:20k, Aug. 30, 2002, pp. 1-6.

Hynynen et al., Temperature Distributions During Local Ultrasound Induced Hyperthermia In Vivo, Ultrasonics Symposium—745 (1982).

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Jeong, K.H., et al., "Neurologic complication associated with intense focused ultrasound". J Cosmet Laser Ther, 2013.

Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).

Kim, H.J., et al., "Coagulation and ablation patterns of high-intensity focused ultrasound on a tissue mimicking phantom and cadaveric skin". Laser Med Sci. Sep. 4, 2015.

Kornstein, A.N., "Ulthera for silicone lip correction". Plast Reconstr Surg, 2012. 129(6): p. 1014e-1015e.

Kornstein, A.N., "Ultherapy shrinks nasal skin after rhinoplasty following failure of conservative measures". Plast Reconstr Surg, 2013. 131(4): p. 664e-6e.

Krischak, G.D., et al., "The effects of non-steroidal anti-inflammatory drug application on incisional wound healing in rats" Journal of Wound Care, vol. 6, No. 2, (Feb. 2007).

Laubach, H.J., et. al., "Confined Thermal Damage with Intense Ultrasound (IUS)" [abstr.] American Society for Laser Medicine and Surgery Abstracts, p. 15 #43 (Apr. 2006).

Laubach, H.J., et. al., "Intense focused ultrasound: evaluation of a new treatment modality for precise microcoagulation within the skin". Dermatol Surg, 2008. 34(5): p. 727-34.

Lee, H.J., et. al., "The efficacy and safety of intense focused ultrasound in the treatment of enlarged facial pores in Asian skin". J Dermatolog Treat, 2014.

Lee, H.S., et. al., "Multiple Pass Ultrasound Tightening of Skin Laxity of the Lower Face and Neck". Dermatol Surg, 2011.

Lin, Sung-Jan, et al., "Monitoring the thermally induced structural transitions of collagen by use of second-harmonic generation microscopy" Optics Letters, vol. 30, No. 6, (Mar. 15, 2005).

MacGregor J.L., et. al., "Microfocused Ultrasound for Skin Tightening". Semin Cutan Med Surg 32:18-25. (2013).

Madersbacher, S. et al., "Tissue Ablation in Benign Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmed Bulk Ablation and Therapy Monitoring Using Intracorporeal Image-Treat Ultrasound Arrays," 4th International Symposium on Therapeutic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling and Experiments," J. Acoust. Soc. Am., Oct. 1, 2005, pp. 2715-2724, vol. 118(4).

Meshkinpour, Azin, et al., "Treatment of Hypertrophic Scars and Keloids With a Radiofrequency Device: A Study of Collagen Effects" Lasers in Surgery and Medicine 37:343-349 (2005).

Minkis, K., et. al., "Ultrasound skin tightening". Dermatol Clin, 2014. 32(1): p. 71-7.

Mitragotri, S., "Healing sound: the use of ultrasound in drug delivery and other therapeutic applications," Nature Reviews; Drug Delivery, pp. 255-260, vol. 4 (Mar. 2005).

Mosser, David M. et al., "Exploring the full spectrum of macrophage activation" Nat Rev Immunol; 8(12): 958-969. (Dec. 2008).

Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).

Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).

Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.

Oni, G., et. al. "Response to 'comments on evaluation of microfocused ultrasound system for improving skin laxity and tightening in the lower face'". Aesthet Surg J. Mar. 2015;35(3):NP83-4.

Oni, G., et. al., "Evaluation of a Microfocused Ultrasound System for Improving Skin Laxity and Tightening in the Lower Face". Aesthet Surg J, 2014. 38:861-868.

Pak, C.S., et. al., "Safety and Efficacy of Ulthera in the Rejuvenation of Aging Lower Eyelids: A Pivotal Clinical Trial". Aesthetic Plast Surg, 2014.

Paradossi et al., "Poly(vinyl alcohol) as versatile biomaterial for potential biomedical applications," Journal of Materials Science: Materials in Medicine, 2003, pp. 687-691, vol. 14.

Pritzker, R.N., et. al, "Updates in noninvasive and minimally invasive skin tightening". Semin Cutan Med Surg. Dec. 2014;33(4):182-7.

Pritzker, R.N., et. al., "Comparison of different technologies for noninvasive skin tightening". Journal of Cosmetic Dermatology, 13, 315-323. (2014).

Rappolee, Daniel A., et al., "Wound Macrophages Express TGF and Other Growth Factors in Vivo: Analysis by mRNA Phenotyping" Science, vol. 241, No. 4866 (Aug. 1988).

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Rokhsar, C., et. al., "Safety and efficacy of microfocused ultrasound in tightening of lax elbow skin". Dermatol Surg. 2015; 41(7):821-6.

Rosenberg, Carol S. "Wound Healing in the Patient with Diabetes Mellitus" Nursing Clinics of North America, vol. 25, No. 1, (Mar. 1990).

Saad et al., "Ultrasound-Enhanced Effects of Adriamycin Against Murine Tumors," Ultrasound in Med. & Biol. vol. 18, No. 8, pp. 715-723 (1992).

Sabet-Peyman, E.J. et. al., "Complications Using Intense Ultrasound Therapy to TreatDeep Dermal Facial Skin and Subcutaneous Tissues". Dermatol Surg 2014; 40:1108-1112.

Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).

Sanghvi, N. T., et al., "Transrectal Ablation of Prostrate Tissue Using Focused Ultrasound," 1993 Ultrasonics Symposium, IEEE, pp. 1207-1210.

Sasaki, G.H. et. al., "Clinical Efficacy and Safety of Focused-Image Ultrasonography: A 2-Year Experience". Aesthet Surg J, 2012.

Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

(56) References Cited

OTHER PUBLICATIONS

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Sklar, L.R. et.al., "Use of transcutaneous ultrasound for lipolysis and skin tightening: a review". Aesthetic Plast Surg, 2014. 38(2): p. 429-41.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 2015 24:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Suh, D.H., et. al., "Intense focused ultrasound tightening in asian skin: clinical and pathologic results". Dermatol Surg, 2011. 37(11): p. 1595-602.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Verhofstad, Michiel H.J. et al., "Collagen Synthesis in rat skin and ileum fibroblasts is affected differently by diabetes-related factors" Int. J. Exp. Path. (1998), 79, 321-328.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
Weiss, M., "Commentary: noninvasive skin tightening: ultrasound and other technologies: where are we in 2011?" Dermatol Surg, 2012. 38(1): p. 28-30.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
Ulthera, Inc., Petition for Inter Partes Review filed Jul. 19, 2016 in Re U.S. Pat. No. 6,113,559; IPR2016-01459; 63 pp. (Filed Jul. 19, 2016).
Ulthera Exhibit 1001, U.S. Pat. No. 6,113,559 to Klopotek, filed Jul. 19, 2016 in re IPR2016-01459.
Ulthera Exhibit 1002, Patent file history of U.S. Pat. No. 6,113,559 Klopotek filed Jul. 19, 2016 in re IPR2016-01459.
Ulthera Exhibit 1003, Declaration of Expert Witness Mark E. Schafer, Ph.D. filed Jul. 19, 2016 in re IPR2016-01459.
Ulthera Exhibit 1004, Curriculum Vitae of Mark E. Schafer, Ph.D. filed Jul. 19, 2016 in re IPR2016-01459.
Ulthera Exhibit 1005, International PCT Publication WO96/34568 Knowlton filed Jul. 19, 2016 in re IPR2016-01459.
Ulthera Exhibit 1006, French Patent No. 2,672,486, Technomed patent filed Jul. 19, 2016 in re IPR2016-01459.
Ulthera Exhibit 1007, English translation of French Patent No. 2,672,486, Technomed filed Jul. 19, 2016 in re IPR2016-01459.
Ulthera Exhibit 1008, International PCT Publication WO93/12742, Technomed PCT filed Jul. 19, 2016 in re IPR2016-01459.
Ulthera Exhibit 1009, English translation of International PCT Publication WO93/12742, Technomed PCT filed Jul. 19, 2016 in re IPR2016-01459.
Ulthera Exhibit 1010, U.S. Pat. No. 5,601,526, which claims priority to Technomed PCT filed Jul. 19, 2016 in re IPR2016-01459.
Ulthera Exhibit 1011, Patent file history for European Patent Application No. 98964890.2, Klopotek filed Jul. 19, 2016 in re IPR2016-01459.
Ulthera Exhibit 1012, Translator Declaration filed Jul. 19, 2016 in re IPR2016-01459.
Ulthera Exhibit 1013, U.S. Pat. No. 5,230,334 to Klopotek filed Jul. 19, 2016 in re IPR2016-01459.
Ulthera Exhibit 1014, U.S. Pat. No. 5,755,753 to Knowlton filed Jul. 19, 2016 in re IPR2016-01459.
Ulthera Exhibit 1015, Excerpts from the American Medical Association Encyclopedia of Medicine (1989) filed Jul. 19, 2016 in re IPR2016-01459.
Ulthera Exhibit 1016, The Simultaneous Study of Light Emissions and Shock Waves Produced by Cavitation Bubbles, G. Gimenez, J. Acoust. Soc. Am. 71(4), Apr. 1982, pp. 839-847 (filed Jul. 19, 2016 in re IPR2016-01459).
Ulthera Exhibit 1017, Excerpts from Gray's Anatomy (1995) (filed Jul. 19, 2016 in re IPR2016-01459).
Ulthera Exhibit 1018, Anatomy of the Superficial Venous System, Comjen G.M., Dermatol. Surg., 1995; 21:35-45 (filed Jul. 19, 2016 in re IPR2016-01459).
Ulthera Exhibit 1019, Section 2.6 from Ultrasonics Theory and Application, by G.L. Gooberman (Hart Publishing Co., 1969) (filed Jul. 19, 2016 in re IPR2016-01459).
Ulthera Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984) (filed Jul. 19, 2016 in re IPR2016-01459).
A Validated Photonumeric Cellulite Severity Scale; Hexsel et al; J Eur Acad Dermatol Venereol. May 2009;23(5):523-8, 6 pages.
Microfocused Ultrasound with Visualization and Calcium Hydroxylapatite for Improving Skin Laxity and Cellulite Appearance; Casabona et al.; Plast Reconstr Surg Glob Open. Jul. 25, 2017;5(7):e1388, 8 pages.
Microfocused Ultrasound With Visualization and Fillers for Increased Neocollagenesis: Clinical and Histological Evaluation;I Casabona et al.; Dermatol Surg. Dec. 2014; 40 Suppl 12:S194-8, 5 pages.

\* cited by examiner

SYSTEM AND METHOD FOR FAT AND CELLULITE REDUCTION

CROSS-REFERENCE TO RELATED APPLICATIONS

This application is a continuation of U.S. patent application Ser. No. 15/374,918 filed Dec. 9, 2016, now U.S. Pat. No. 9,707,412, which is a continuation of U.S. application Ser. No. 15/041,829 filed Feb. 11, 2016, now U.S. Pat. No. 9,522,290, which is a continuation of U.S. application Ser. No. 14/550,720 filed Nov. 21, 2014, now U.S. Pat. No. 9,283,410, which is a continuation of U.S. application Ser. No. 14/164,598 filed Jan. 27, 2014, now U.S. Pat. No. 8,915,854, which is a continuation of U.S. application Ser. No. 13/789,562 filed Mar. 7, 2013, now U.S. Pat. No. 8,636,665, which is a continuation of U.S. application Ser. No. 13/356,405 filed Jan. 23, 2012, now U.S. Pat. No. 8,672,848, which is a continuation of U.S. application Ser. No. 11/163,154 filed on Oct. 6, 2005, now U.S. Pat. No. 8,133,180, which claims the benefit of priority to U.S. Provisional No. 60/616,753, filed on Oct. 6, 2004, each of which are hereby incorporated by reference in their entirety herein. Any and all priority claims identified in the Application Data Sheet, or any correction thereto, are hereby incorporated by reference under 37 CFR 1.57.

BACKGROUND

Field of the Invention

The present invention relates to ultrasound therapy systems, and in particular to a method and system for treating cellulite.

Description of the Related Art

Cellulite is a common skin disorder that appears as an irregularity of skin contour, often characterized by a dimple appearance of the skin. This condition affects 80% of women worldwide and tends to gather superficially around the thighs, hips, and buttocks.

Cellulite develops in the body when fat is deposited immediately below the dermis and contained in fat chambers (lobuli) that can become swollen. As the fat cells grow in size, lobuli tend to protrude into a dermis layer, surrounding tissue becomes compressed and hardened, making blood circulation more difficult in trapping fluids. Reduced elasticity of the adipose tissue produces an undesirable tension between the layers. The resulting protrusions and depressions of connective tissue anchor points create the appearance of cellulite.

This condition responds with varying results to invasive procedures, such as liposuction. The non-invasive technologies such as massagers, and low frequency ultrasound diathermy, show marginal results. Preliminary results shown by combination of infrared light and RF energy have some promise of improving skin contours, but significant progress is needed.

SUMMARY

In accordance with various aspects of the present invention, a method and system for non-invasive treatment of cellulite with ultrasound are provided. An exemplary treatment method and system comprises a therapeutic ultrasound system for providing ultrasound treatment to a deep tissue region that contains a lower part of dermis and proximal protrusions of fat lobuli into the dermis. Such an exemplary treatment system delivers conformal ultrasound therapeutic energy to the region creating a thermal injury and coagulating the proximal protrusions of fat lobuli, thereby eliminating the fat protrusions into the dermis the dermis resulting in improved appearance of the overlaying superficial layers of the skin. In accordance with exemplary embodiments, an exemplary treatment system may include ultrasound imaging mechanisms using the same or a separate probe before, after or during the treatment. Other imaging configurations can be utilized to image, monitor, and provide feedback of ultrasound therapy, such as MRI, X-Ray, PET, infrared or others.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

Figure 1:
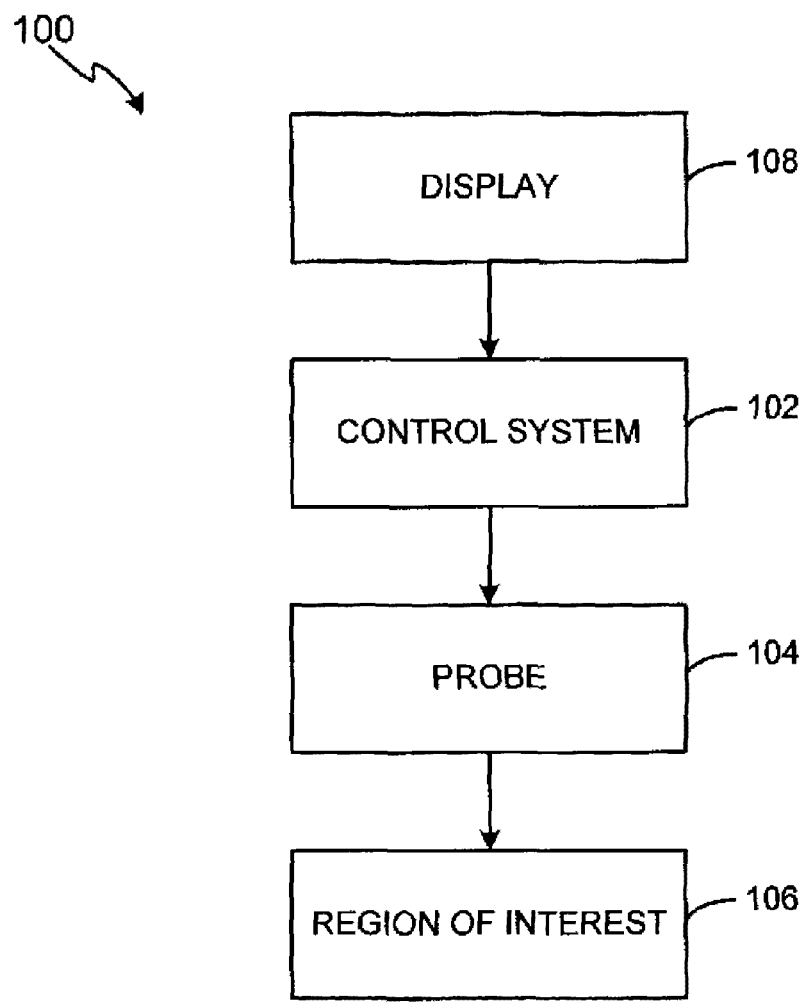
FIG. 1 illustrates a block diagram of an exemplary ultrasound treatment system for treating cellulite in accordance with an exemplary embodiment of the present invention.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a non-invasive cellulite treatment system as described herein are merely indicative of exemplary applications for the invention. For example, the principles, features and methods discussed may be applied to any medical application. Further, various aspects of the present invention may be suitably applied to other applications.

In accordance with various aspects of the present invention, a non-invasive method and system for treating cellulite are provided. For example, in accordance with an exemplary embodiment, with reference to FIG. 1, an exemplary treatment system 100 configured to treat a region of interest 106 comprises a control system 102, an imaging/therapy probe with acoustic coupling 104, and a display system 108.

Control system 102 and display system 108 can comprise various configurations for controlling probe 104 and overall system 100 functionality, such as, for example, a microprocessor with software and a plurality of input/output devices, system and devices for controlling electronic and/or mechanical scanning and/or multiplexing of transducers, a system for power delivery, systems for monitoring, systems for sensing the spatial position of the probe and/or transducers, and/or systems for handling user input and recording treatment results, among others. Imaging/therapy probe 104 can comprise various probe and/or transducer configurations. For example, probe 104 can be configured for a combined dual-mode imaging/therapy transducer, coupled or co-housed imaging/therapy transducers, or simply a separate therapy probe and an imaging probe.

In accordance with an exemplary embodiment, treatment system 100 is configured for treating a deep tissue region that contains a lower part of dermis and proximal protrusions of fat lobuli into the dermis, by first, imaging of region of interest 106 for localization of the treatment area and surrounding structures, second, delivery of ultrasound energy at a depth, distribution, timing, and energy level to achieve the desired therapeutic effect, and third to monitor the treatment area before, during, and after therapy to plan and assess the results and/or provide feedback. As to the delivery of energy, control system 102 and transducer system 102 can be suitably configured to deliver conformal ultrasound therapeutic energy to ROI 106 creating a thermal injury and coagulating the proximal protrusions of fat lobuli, thereby eliminating the fat protrusions into the dermis. As used herein, the term "dermis" refers to any part of the dermis and/or the epidermis.

In addition, by treatment of ROI 106, transducer system 102 may be configured to deliver one or more energy fields to promote one or more effects, for example, ablation of existing tissue, the breaking up of fat cell clusters, stretching of the fibrous bonds, enhancement of lymphatic drainage, stimulation of the evacuation of fat decay products, and/or enhanced cell permeability in order to treat cellulite.

Figure 2:
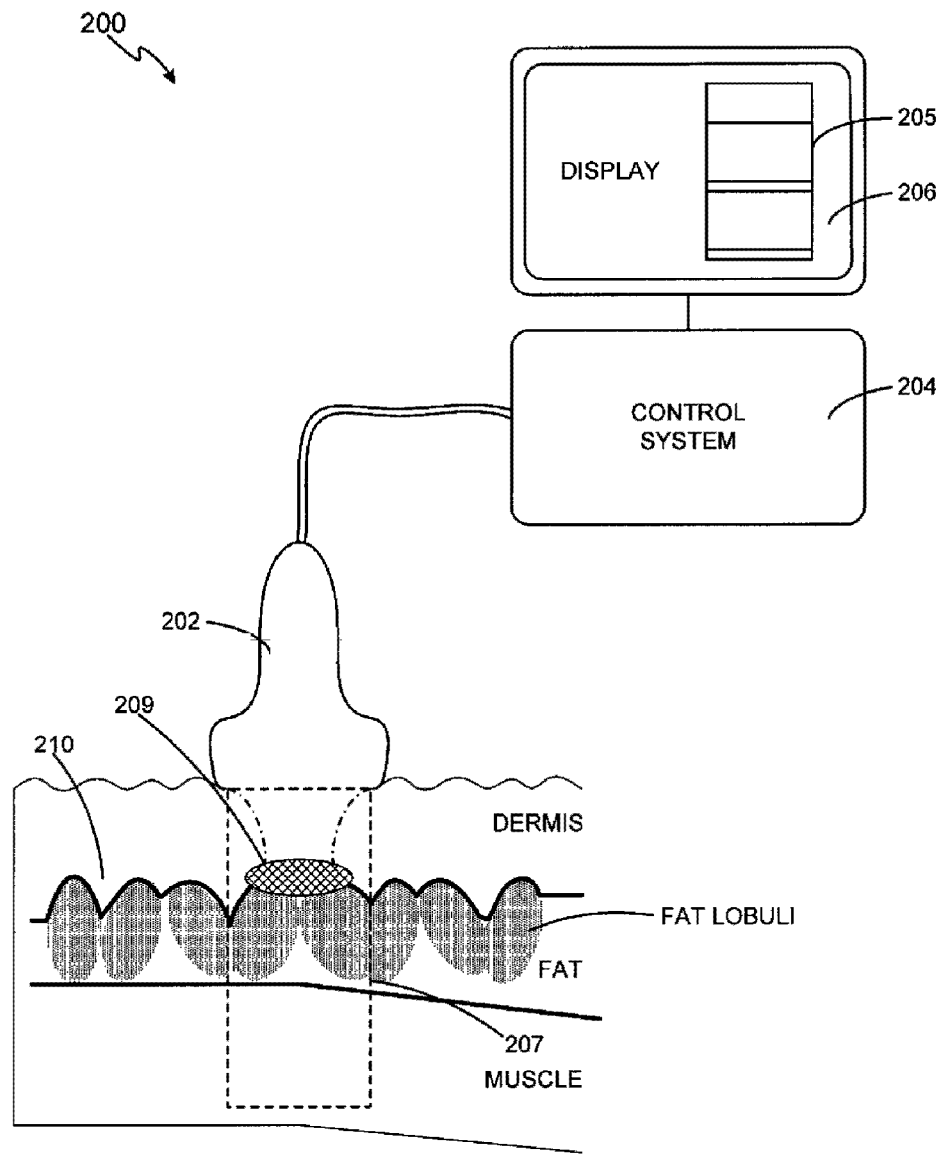
FIG. 2 illustrates a cross sectional diagram of an exemplary probe system in accordance with exemplary embodiments of the present invention.

An exemplary ultrasound therapy system of FIG. 1 is further illustrated in an exemplary embodiment in FIG. 2. A therapy transducer system 200 includes a transducer probe 202 connected to a control system 204, and display 206, in combination may provide therapy, imaging, and/or temperature or other tissue parameters monitoring to region of interest 210. Exemplary transducer system 200 is configured for first, imaging and display of region of interest 210 for localization of the treatment area and surrounding structures, second, delivery of focused, unfocused, or defocused ultrasound energy at a depth, distribution, timing, and energy level to achieve the desired therapeutic effect of thermal ablation to treat cellulite, and third to monitor the treatment area and surrounding structures before, during, and after therapy to plan and assess the results and/or provide feedback to control system 204 and/or an operator.

Exemplary transducer probe 202 can be configured to be suitably controlled and/or operated in various manners. For example, transducer probe 202 may be configured for use within an ultrasound treatment system, an ultrasound imaging system and/or an ultrasound imaging, therapy, and/or treatment monitoring system, including motion control subsystems.

Control system 204 can be configured with one or more subsystems, processors, input devices, displays and/or the like. Display 206 may be configured to image and/or monitor ROI 210 and/or any particular sub-region within ROI 210. Display 206 can be configured for two-dimensional, three-dimensional, real-time, analog, digital and/or any other type of imaging. Exemplary embodiments of both control system 204 and display 206 are described in greater detail herein.

Region of interest 210, can be comprised of superficial layer (epidermis/dermis) subcutaneous fat, lobuli, and muscle. Exemplary transducer system 200, is configured to provide cross-sectional two-dimensional imaging of the region 207, displayed as an image 205, with a controlled thermal lesion 209, confined approximately to proximal portion of fat lobuli and lower portion of dermis.

Transducer system 200 can be configured with the ability to controllably produce conformal treatment areas in superficial human tissue within region of interest 210 through precise spatial and temporal control of acoustic energy deposition. In accordance with an exemplary embodiment, control system 204 and transducer probe 202 can be suitably configured for spatial control of the acoustic energy by controlling the manner of distribution of the acoustical energy. For example, spatial control may be realized through selection of the type of one or more transducer configurations insonifying region of interest 210, selection of the placement and location of transducer probe 202 for delivery of acoustical energy relative to region-of-interest 210, e.g., transducer probe 202 configured for scanning over part or whole of region-of-interest 210 to deliver conformal ultrasound therapeutic energy to create a thermal injury and to coagulate the proximal protrusions of fat lobuli, thereby eliminating the fat protrusions into the dermis. Transducer probe 202 may also be configured for control of other environment parameters, e.g., the temperature at the acoustic coupling interface can be controlled. In addition to the spatial control, control system 204 and/or transducer probe 202 can also be configured for temporal control, such as through adjustment and optimization of drive amplitude levels, frequency/waveform selections, and timing sequences and other energy drive characteristics to control the treatment of tissue. The spatial and/or temporal control can also be facilitated through open-loop and closed-loop feedback arrangements, such as through the monitoring of various positional and temporal characteristics. For example, through such spatial and/or temporal control, an exemplary treatment system 200 can enable the regions of thermal injury to possess arbitrary shape and size and allow the tissue to be treated in a controlled manner.

Transducer system 200 may be used to provide a mechanical action of ultrasound to physically break fat cell clusters and stretch the fibrous bonds. This mechanical action will also enhance lymphatic drainage, stimulating the evacuation of fat decay products. That is, the ultrasound may facilitate movement of the muscles and soft tissues within ROI 210, thereby facilitating the loosening of fat deposits and/or the break up of fibrous tissue surrounding fat deposits.

In addition, transducer system 200 can be configured to deliver various therapeutic levels of ultrasound to increase the speed at which fat metabolizes, according to the Arrhenius Law: $Y=Ae^{-B/T}$, where Y is the yield of metabolic reaction, A and B are constants, and T is the temperature in degrees Kelvin. In one exemplary embodiment, transducer system 200 is configured to provide various therapeutic levels of ultrasound to increase the speed at which fat metabolizes. That is, according to Arrhenius Law, the yield, Y of a metabolic reaction is a function of temperature, T: $Y=Ae^{-B/T}$, where A and B are constants, and T is the temperature in degrees Kelvin. Thus, ultrasound treatment from transducer system 200, ranging from approximately 750 kHz to 20 MHz, can increase the temperature in a treatment area, thereby increasing the metabolic reaction yield for that treatment area.

Figure 3A:
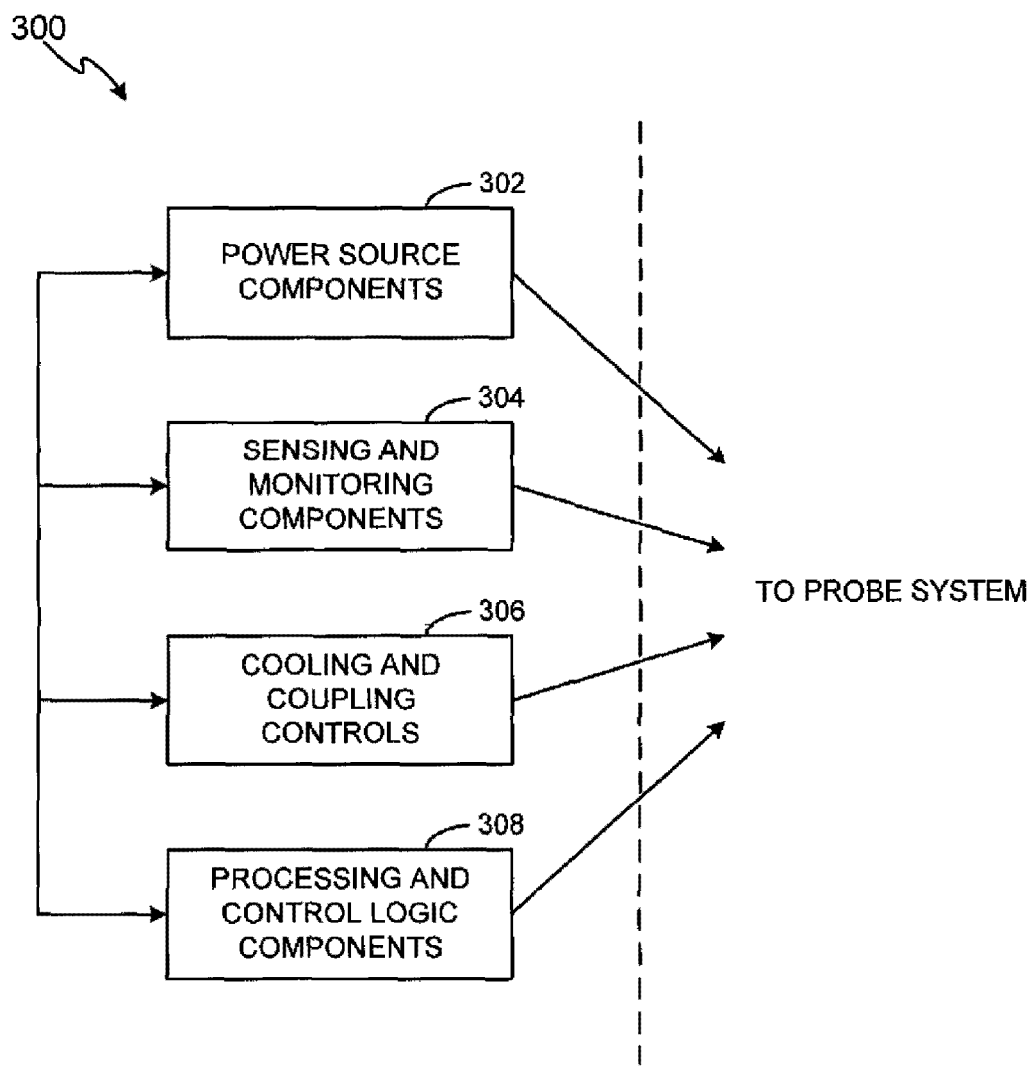
FIGS. 3A and 3B illustrate block diagrams of an exemplary control system in accordance with exemplary embodiments of the present invention.
Figure 3B:
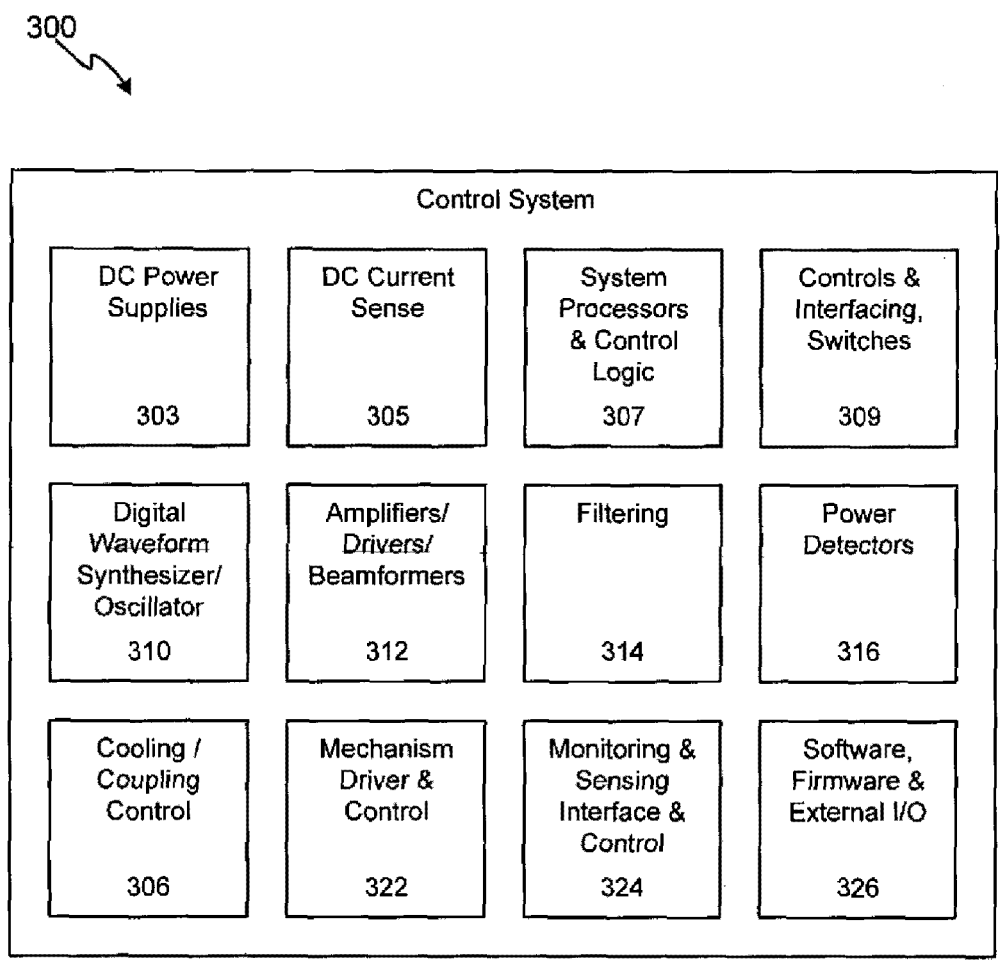

As previously described, control systems 104 and 204 may be configured in various manners with various subsystems and subcomponents. With reference to FIGS. 3A and 3B, in accordance with exemplary embodiments, an exemplary control system 300 can be configured for coordination and control of the entire therapeutic treatment process in accordance with the adjustable settings made by a therapeutic treatment system user. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for cellulite treatment, and the embodiment in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems 322 implemented within transducer probe 104 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 100.

For example, In such an open-loop system, a system user can suitably monitor the imaging and/or other spatial or temporal parameters and then adjust or modify same to accomplish a particular treatment objective. Instead of, or in combination with open-loop feedback configurations, an exemplary treatment system can comprise a closed-loop feedback system, wherein images and/or spatial/temporal parameters can be suitably monitored within monitoring component to generate signals.

During operation of exemplary treatment system 100, a lesion configuration of a selected size, shape, orientation is determined. Based on that lesion configuration, one or more spatial parameters are selected, along with suitable temporal parameters, the combination of which yields the desired conformal lesion. Operation of the transducer can then be initiated to provide the conformal lesion or lesions. Open and/or closed-loop feedback systems can also be implemented to monitor the spatial and/or temporal characteristics, and/or other tissue parameter monitoring, to further control the conformal lesions.

Cooling/coupling control systems 306 may be provided to remove waste heat from exemplary probe 104, provide a controlled temperature at the superficial tissue interface and deeper into tissue, and/or provide acoustic coupling from transducer probe 104 to region-of-interest 106. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 104 can also be configured in various manners and comprise a number of reusable and/or disposable components and parts in various embodiments to facilitate its operation. For example, transducer probe 104 can be configured within any type of transducer probe housing or arrangement for facilitating the coupling of transducer to a tissue interface, with such housing comprising various shapes, contours and configurations depending on the particular treatment application. For example, in accordance with an exemplary embodiment, transducer probe 104 can be depressed against a tissue interface whereby blood perfusion is partially or wholly cut-off, and tissue flattened in superficial treatment region-of-interest 106. Transducer probe 104 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 104 may also comprise cables and connectors; motion mechanisms, motion sensors and encoders; thermal monitoring sensors; and/or user control and status related switches, and indicators such as LEDs. For example, a motion mechanism in probe 104 may be used to controllably create multiple lesions, or sensing of probe motion itself may be used to controllably create multiple lesions and/or stop creation of lesions, e.g. for safety reasons if probe 104 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
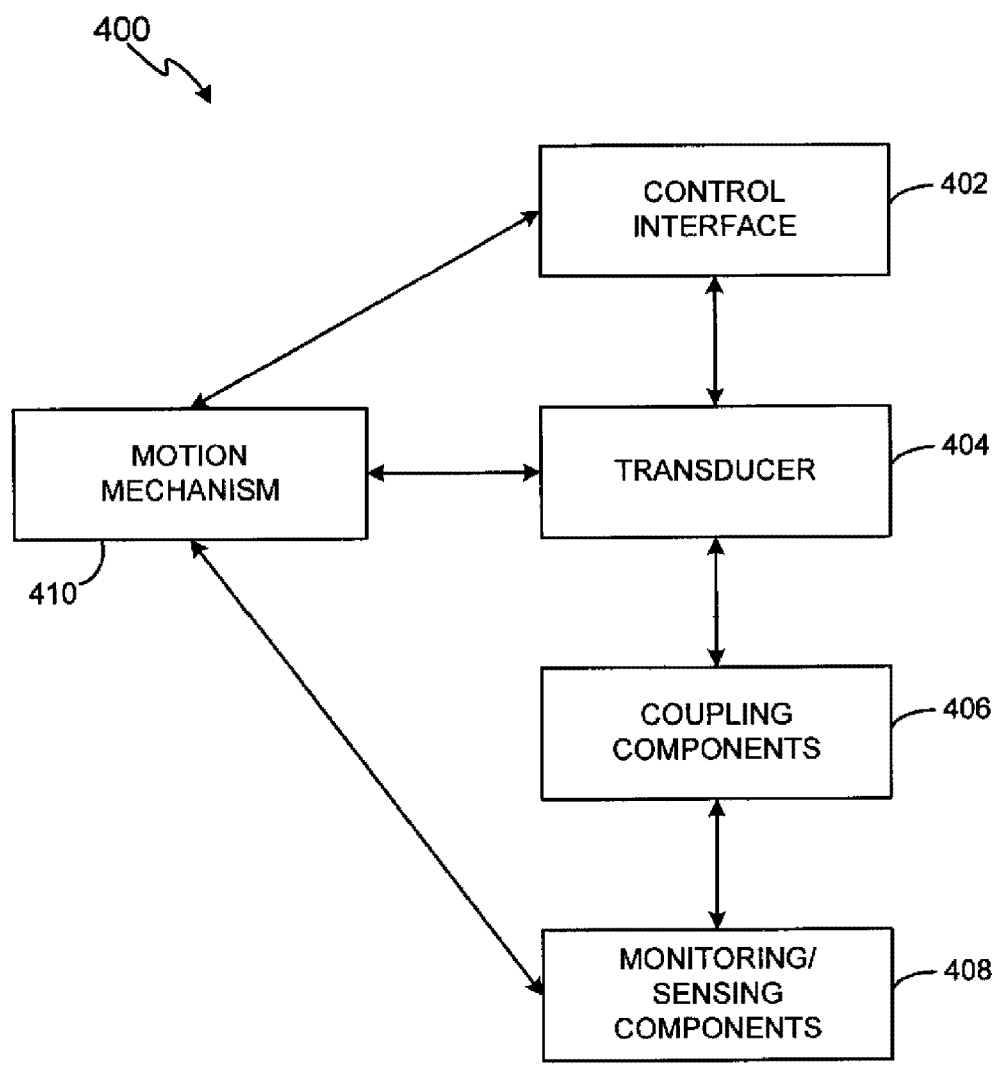
FIGS. 4A and 4B illustrate block diagrams of an exemplary probe system in accordance with exemplary embodiments of the present invention.
Figure 4B:
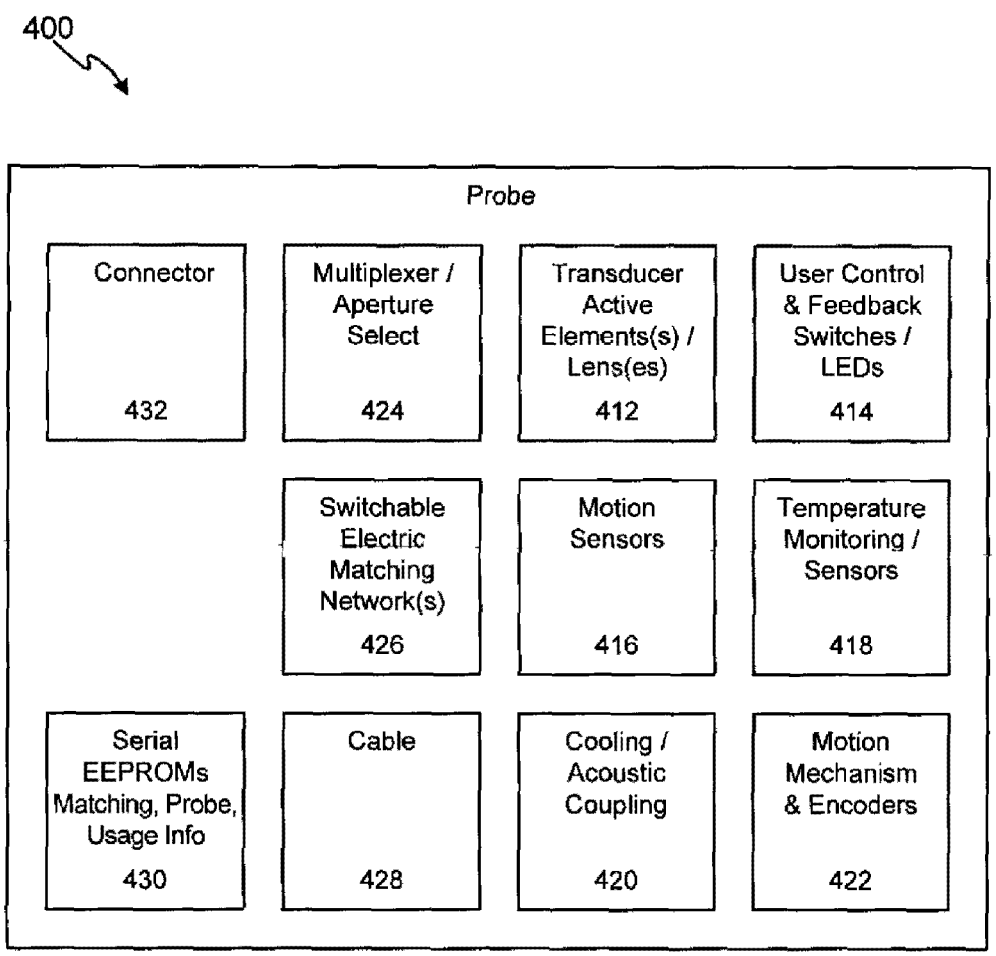

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide ultrasound energy for cellulite treatment, and the embodiment in FIGS. 4A and 4B are merely for illustration purposes.

In accordance with an exemplary embodiment of the present invention, transducer probe 400 is configured to deliver energy over varying temporal and/or spatial distributions in order to provide energy effects and initiate responses in a region of interest. These effects can include, for example, thermal, cavitational, hydrodynamic, and resonance induced tissue effects. For example, exemplary transducer probe 400 can be operated under one or more frequency ranges to provide two or more energy effects and initiate one or more responses in the region of interest. In addition, transducer probe 400 can also be configured to deliver planar, defocused and/or focused energy to a region of interest to provide two or more energy effects and to initiate one or more reactions. These responses can include, for example, diathermy, hemostasis, revascularization, angiogenesis, growth of interconnective tissue, tissue reformation, ablation of existing tissue, protein synthesis and/or enhanced cell permeability. These and various other exemplary embodiments for such combined ultrasound treatment, effects and responses are more fully set forth in U.S. patent application Ser. No. 10/950,112, entitled "METHOD AND SYSTEM FOR COMBINED ULTRASOUND TREATMENT," Filed Sep. 24, 2004 and incorporated herein by reference.

Control interface 402 is configured for interfacing 428 with control system 300 to facilitate control of transducer probe 400. Control interface components 402 can comprise multiplexer/aperture select 424, switchable electric matching networks 426, serial EEPROMs and/or other processing components and matching and probe usage information 430 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond and beyond and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
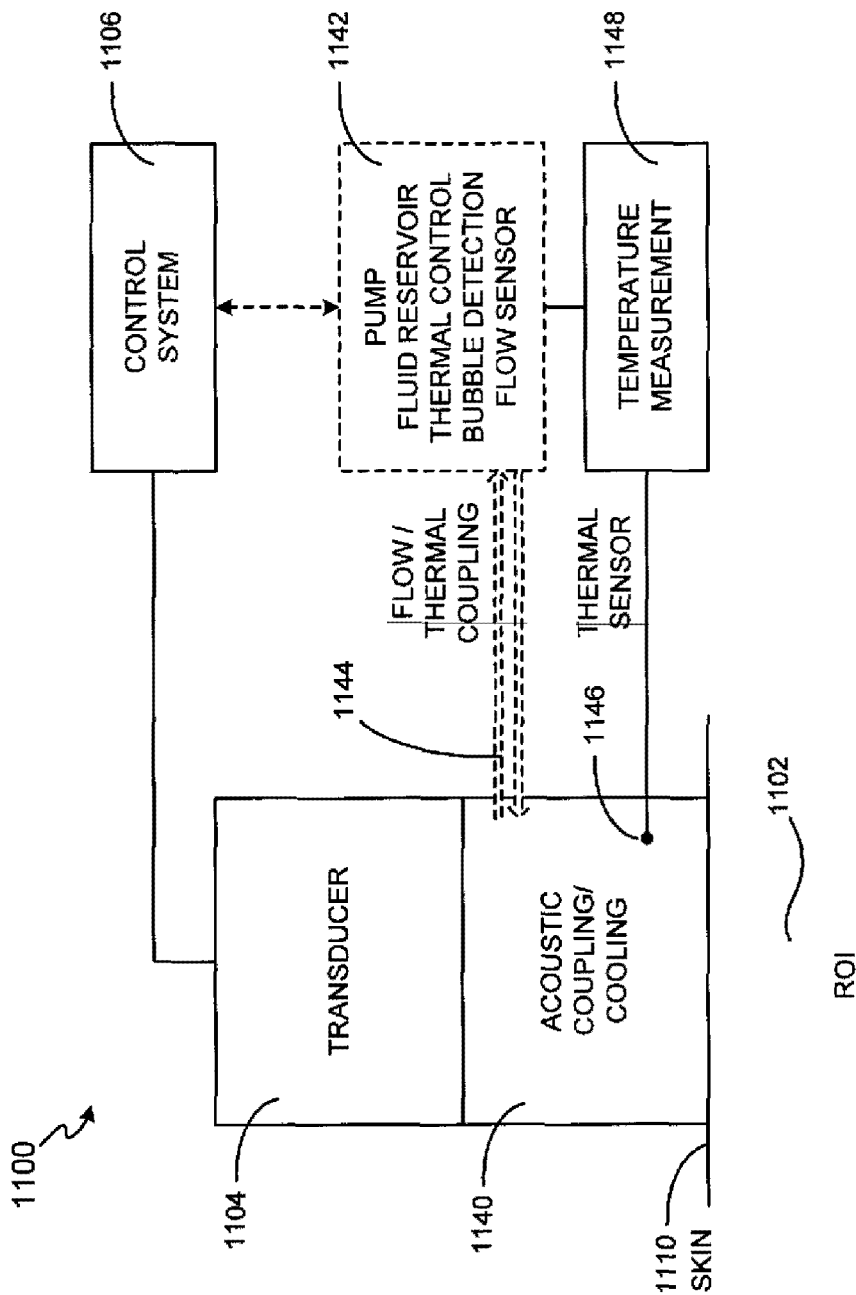
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer 1104 to and from the region of interest 1102, to provide thermal control at the probe 1100 to region-of-interest interface 1110, and to remove potential waste heat from the transducer probe at region 1144. Temperature monitoring can be provided at the coupling interface via a thermal sensor 1146 to provide a mechanism of temperature measurement 1148 and control via control system 1106 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

Monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism 422 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for producing conformal lesions of thermal injury in superficial human tissue within a region of interest through precise spatial and temporal control of acoustic energy deposition. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of a lower range, for example from approximately 750 kHz to 5 MHz. Transduction element 404 can also be configured with a second thickness selected to provide a center operating frequency of a higher range, for example from approximately 5 MHz to 20 MHz or more. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range. For example, transducer 404 can comprise a first transducer configured with a first transduction element having a thickness corresponding to a center frequency range of approximately 750 kHz to 5 MHz, and a second transducer configured with a second transduction element having a thickness corresponding to a center frequency of approximately 5 MHz to 20 MHz or more.

Figure 5:
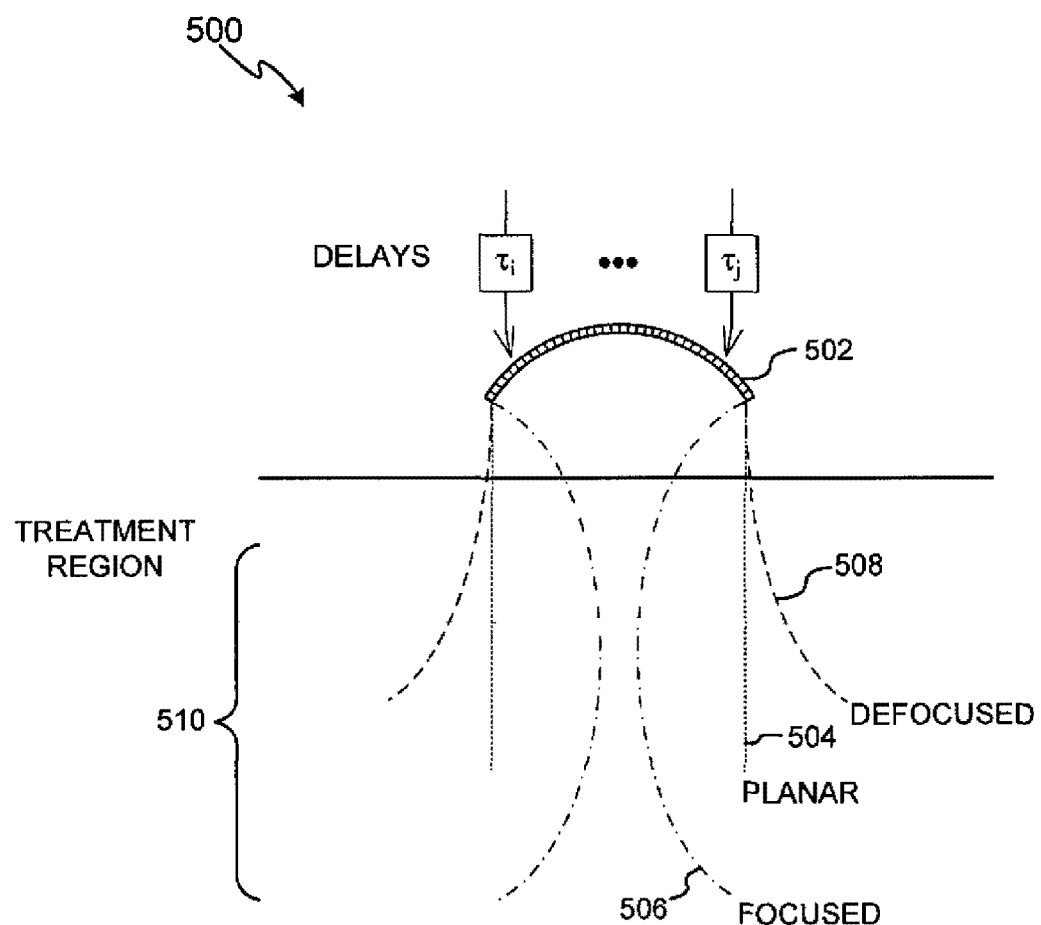
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and/or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 604 in combination with one or more transduction elements 606 to facilitate increased flexibility in treating ROI 610. Array 602 may be configured in a manner similar to transducer 502. That is, array 602 can be configured as an array 604 of electronic apertures that may be operated by a variety of phases via variable electronic time delays, for example, $T_1$, $T_2$ . . . $T_j$. By the term "operated," the electronic apertures of array 604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
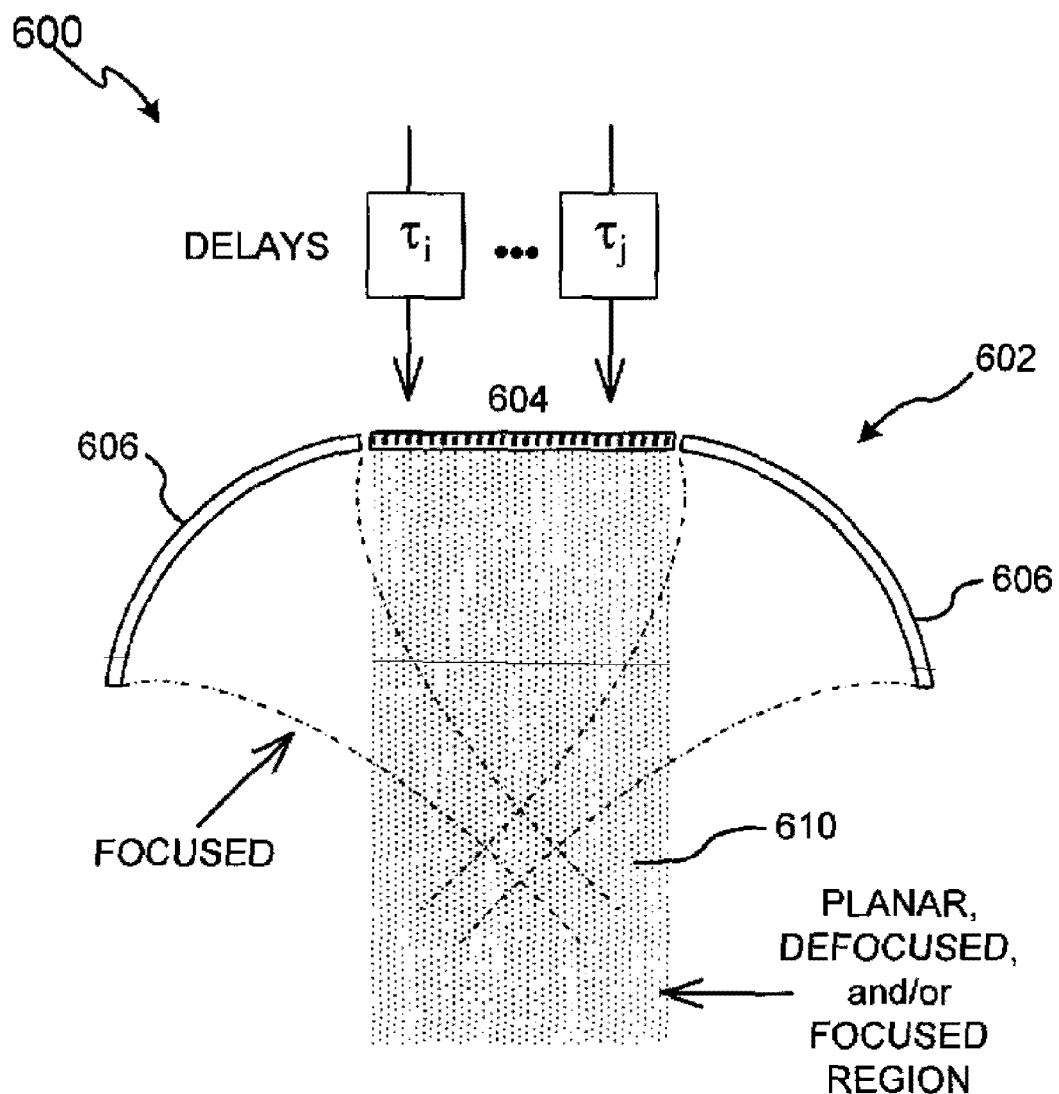
FIGS. 6A and 6B illustrate cross-sectional diagrams of an exemplary transducer in accordance with exemplary embodiments of the present invention.
Figure 6B:
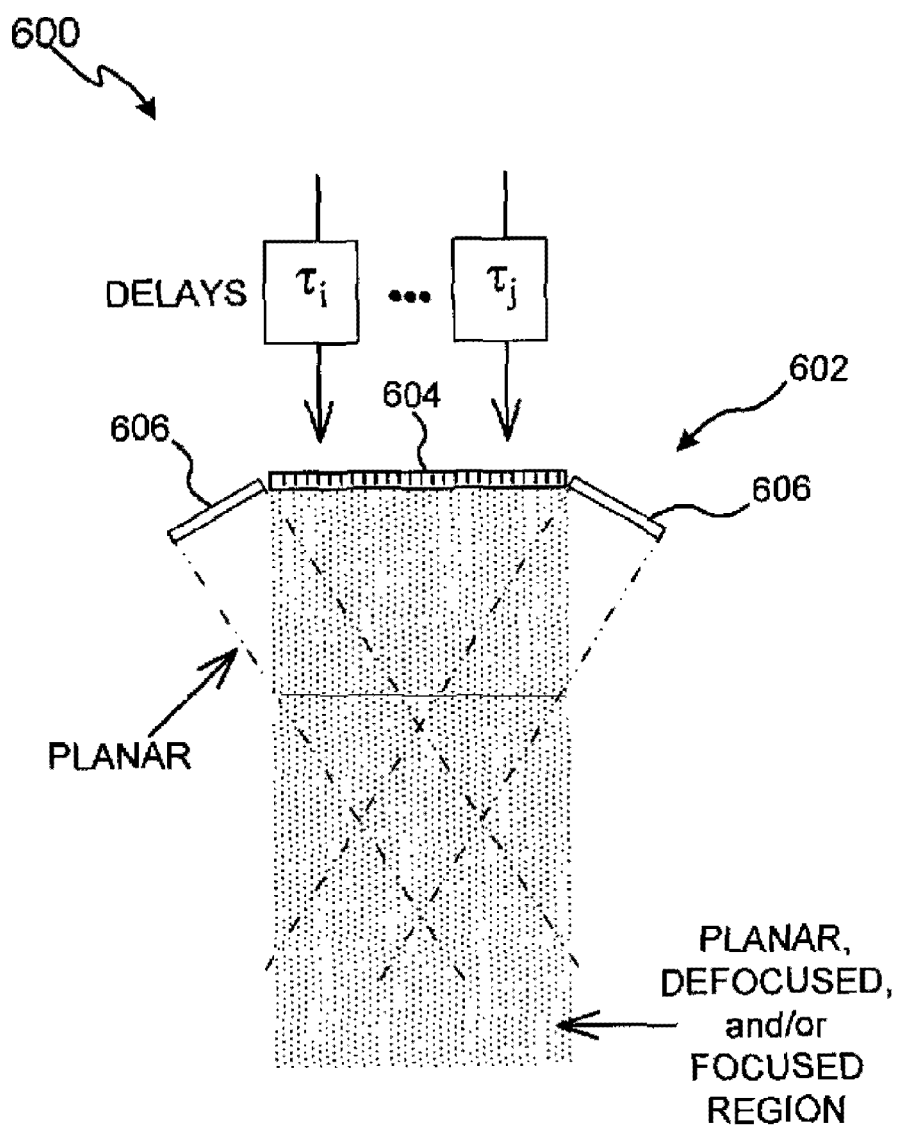

In another exemplary embodiment, depicted in FIG. 6B, transduction elements 606 can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
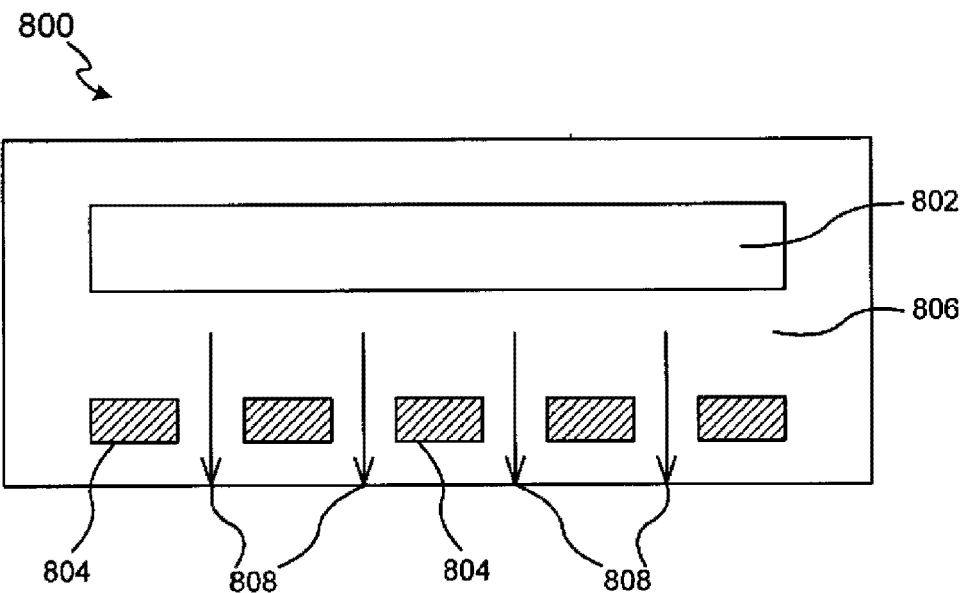
FIGS. 8A and 8B illustrate cross-sectional diagrams of an exemplary transducer in accordance with another exemplary embodiment of the present invention.
Figure 8B:
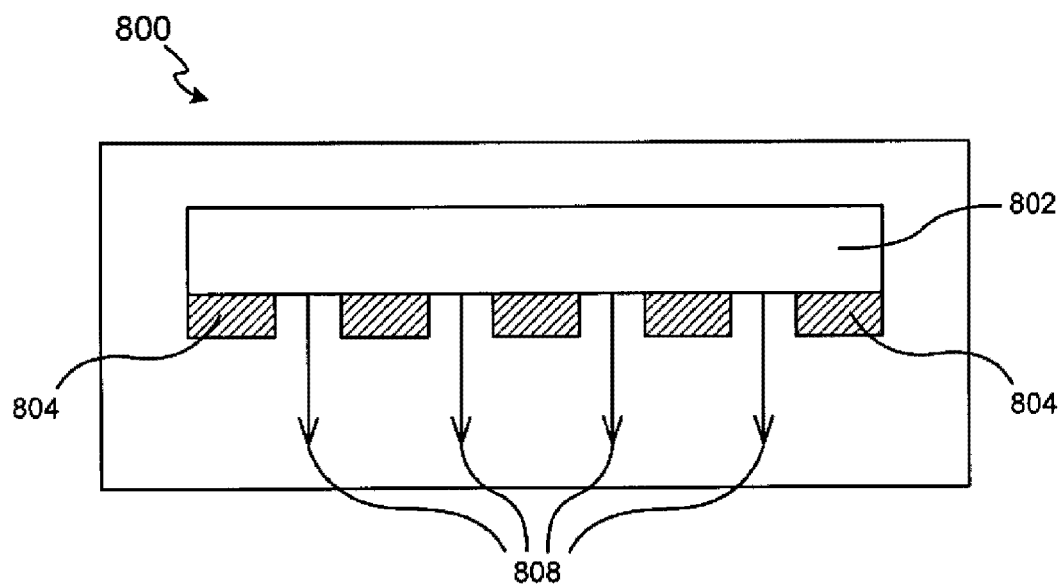

With reference to FIGS. 8A and 8B, transducer 800 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
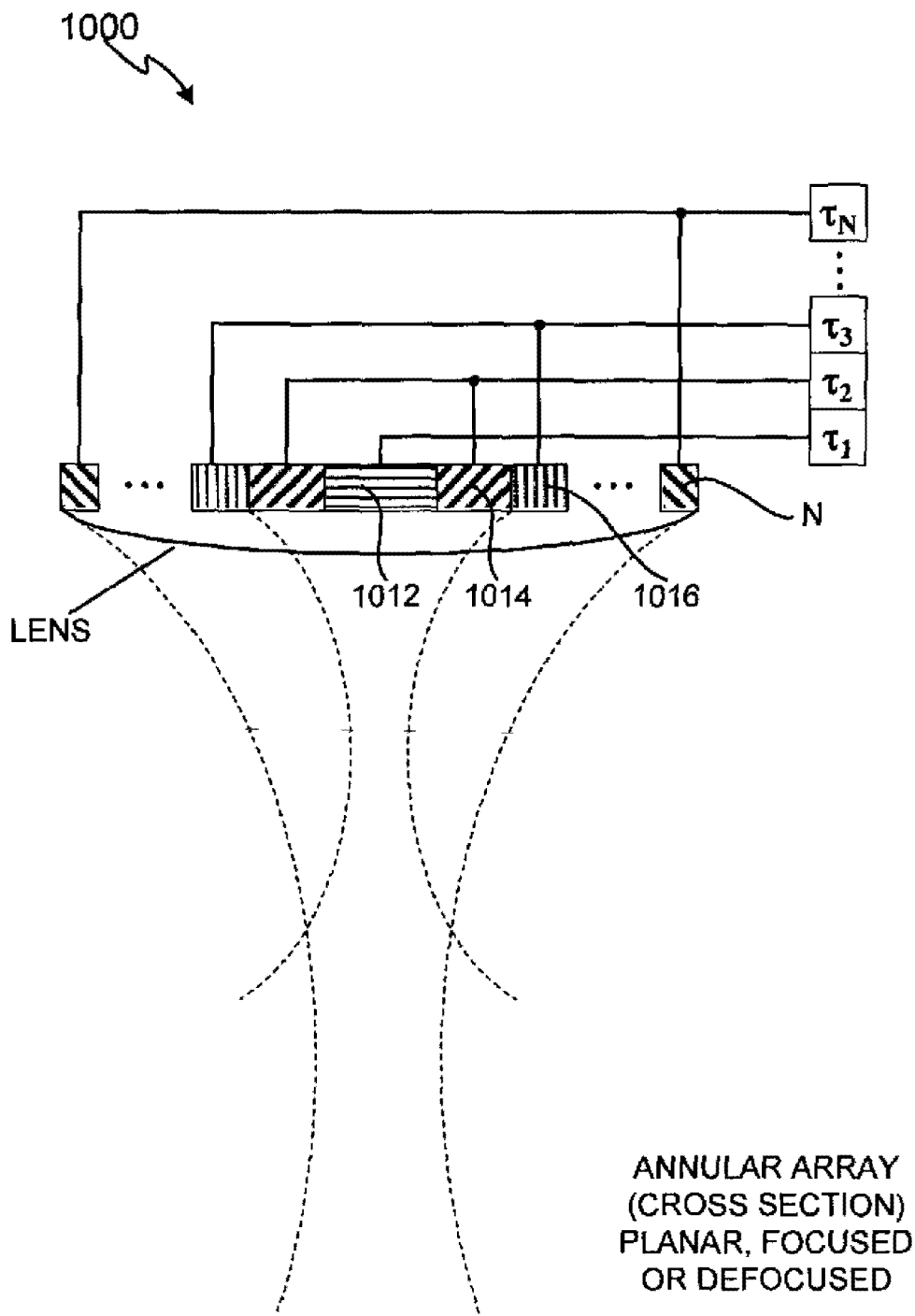
FIGS. 10A-10F illustrate cross-sectional diagrams of exemplary transducers in accordance with other exemplary embodiments of the present invention.
Figure 10B:
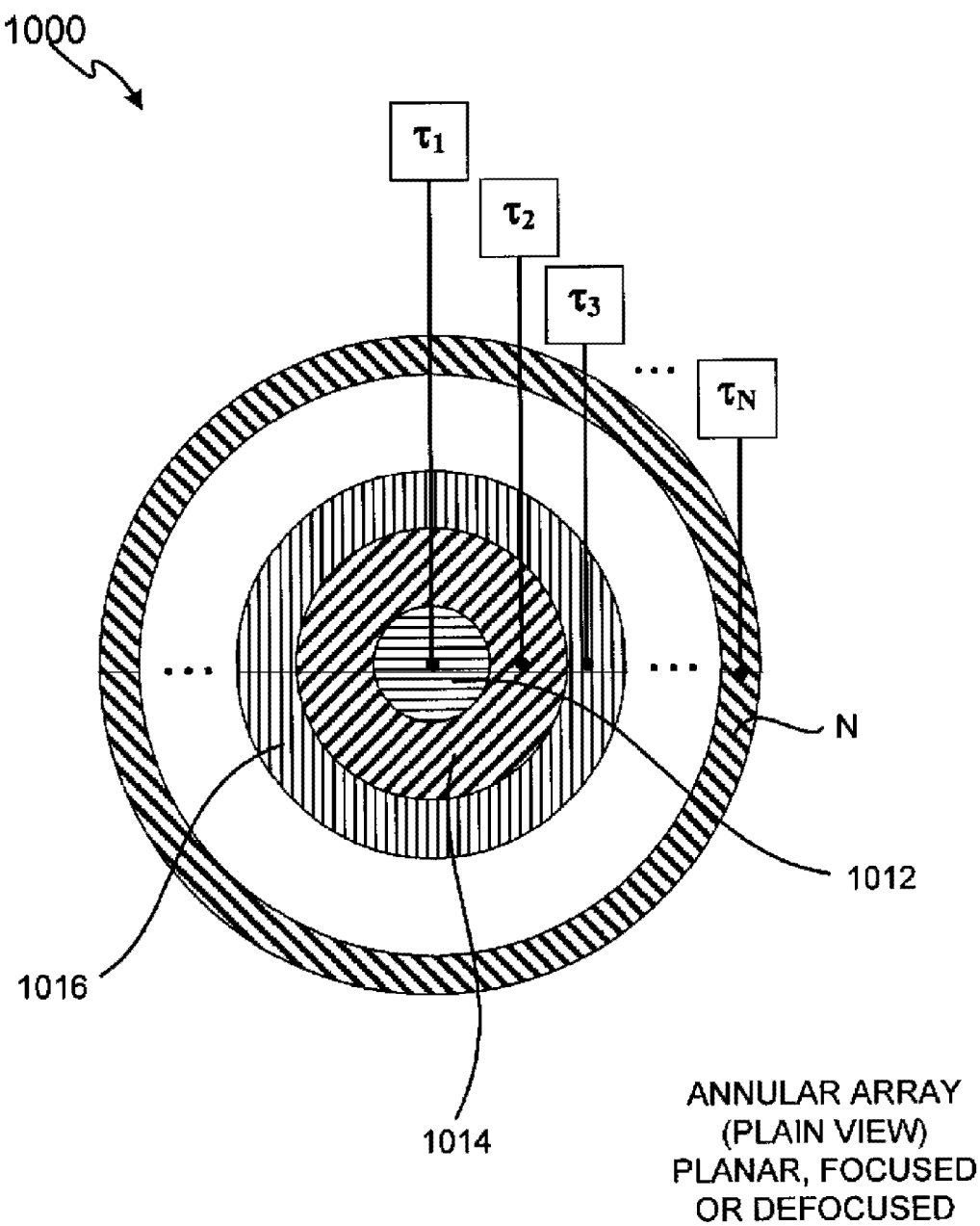
Figure 10C:
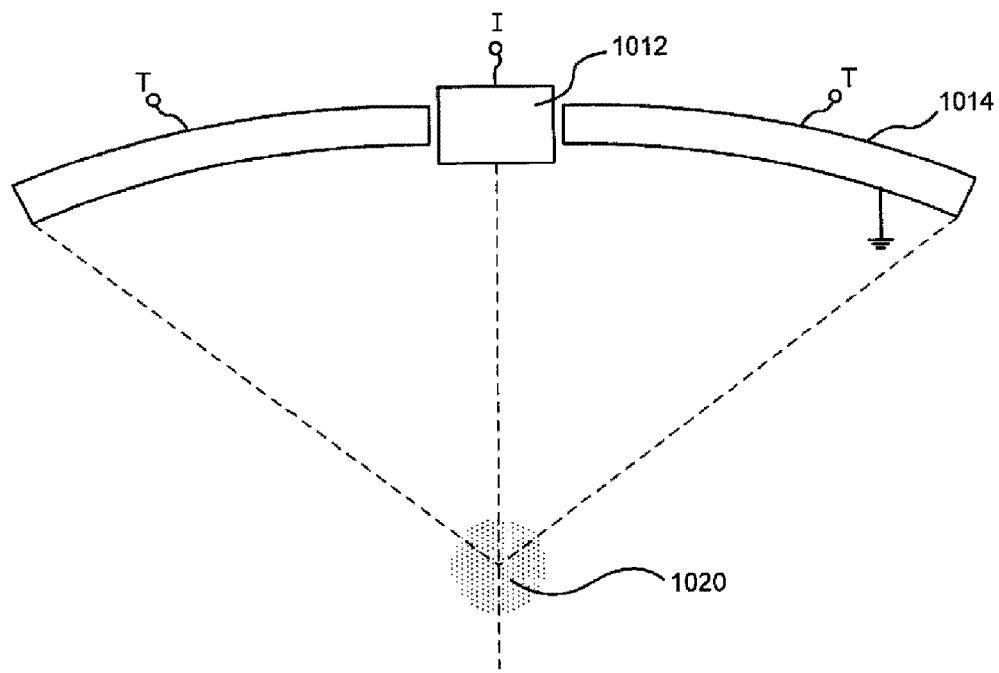
Figure 10D:
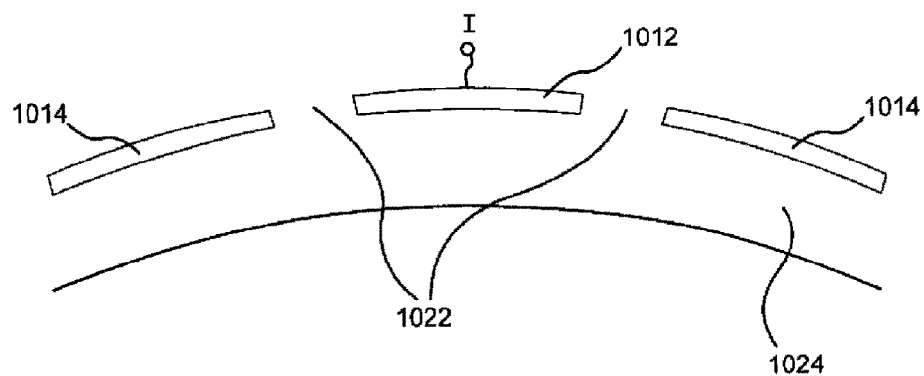
Figure 10E:
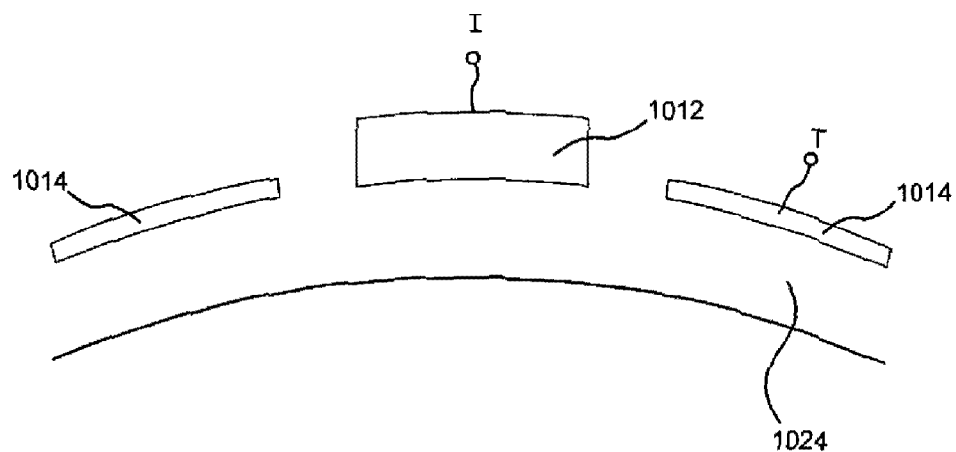

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $\tau_1, \tau_2, \tau_3 \ldots \tau_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 1000 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with another aspect of the invention, transducer probe 400 may be configured to provide one, two or three-dimensional treatment applications for focusing acoustic energy to one or more regions of interest. For example, as discussed above, transducer probe 400 can be suitably diced to form a one-dimensional array, e.g., a transducer comprising a single array of sub-transduction elements.

Figure 9:
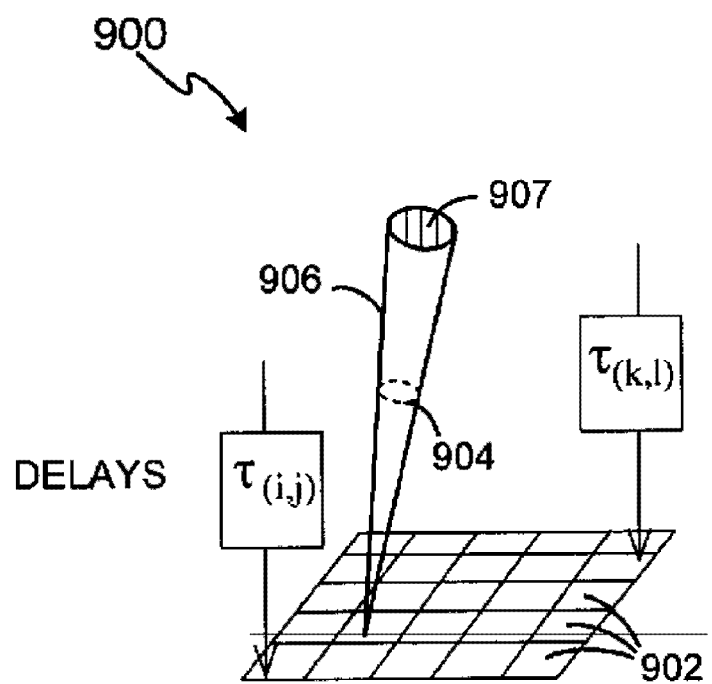
FIG. 9 illustrates an exemplary transducer configured as a two-dimensional array for ultrasound treatment in accordance with an exemplary embodiment of the present invention.

In accordance with another exemplary embodiment, transducer probe 400 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904 of the treatment region. As a result, the two-dimensional array 900 can provide a two-dimensional slicing of the image place of a treatment region, thus providing two-dimensional treatment.

In accordance with another exemplary embodiment, transducer probe 400 may be suitably configured to provide three-dimensional treatment. For example, to provide three dimensional treatment of a region of interest, with reference again to FIG. 3, a three-dimensional system can comprise transducer probe 400 configured with an adaptive algorithm, such as, for example, one utilizing three-dimensional graphic software, contained in a control system, such as control system 300. The adaptive algorithm is suitably configured to receive two-dimensional imaging, temperature and/or treatment information relating to the region of interest, process the received information, and then provide corresponding three-dimensional imaging, temperature and/ or treatment information.

In accordance with an exemplary embodiment, with reference again to FIG. 9, an exemplary three-dimensional system can comprise a two-dimensional array 900 configured with an adaptive algorithm to suitably receive slices 904, 907 from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

Alternatively, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
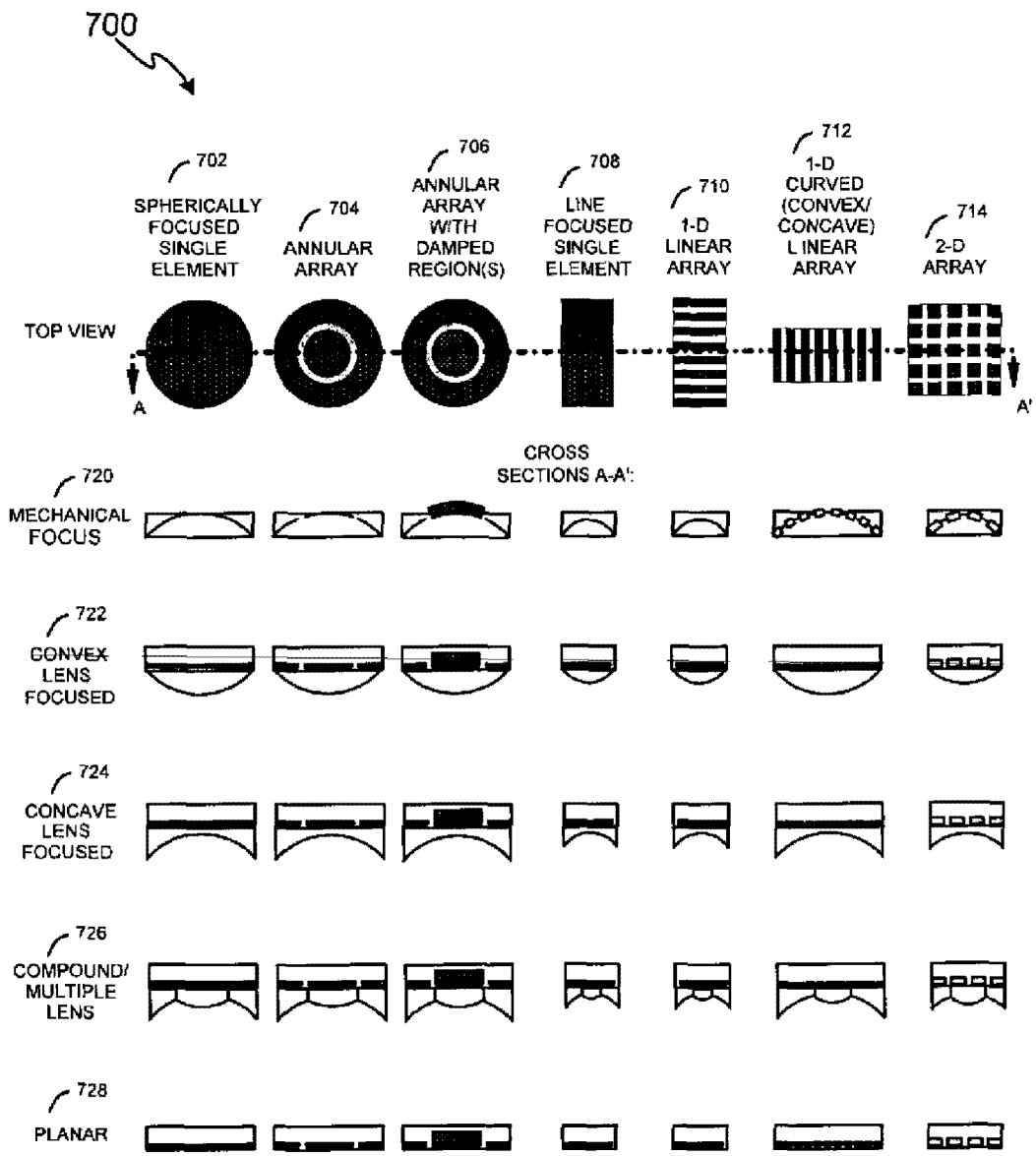
FIG. 7 illustrates exemplary transducer configurations for ultrasound treatment in accordance with various exemplary embodiments of the present invention.
Figure 10F:
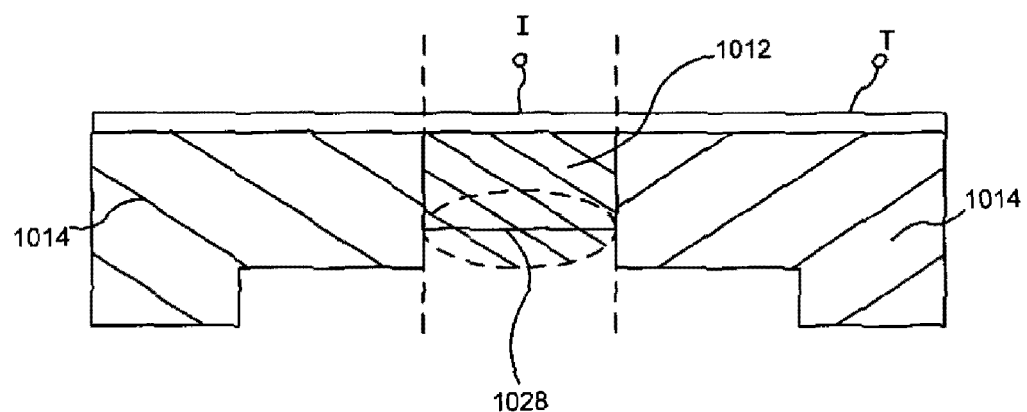

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays 712 in concave or convex form, with or without elevation focusing, 2-D arrays 714, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Various shaped treatment lesions can be produced using the various acoustic lenses and designs in FIGS. 10A-10F. For example, mushroom shaped lesions may be produced from a spherically focused source, and/or planar lesions from a flat source. That is, as the application of ablative ultrasound energy continues, this causes thermal expansion to generate a growing lesion. Concave planar sources and arrays can produce a "V-shaped" or ellipsoidal lesion. Electronic arrays, such as a linear array, can produce defocused, planar, or focused acoustic beams that may be employed to form a wide variety of additional lesion shapes at various depths. An array may be employed alone or in conjunction with one or more planar or focused transducers. Such transducers and arrays in combination produce a very wide range of acoustic fields and their associated benefits. A fixed focus and/or variable focus lens or lenses may be used to further increase treatment flexibility. A convex-shaped lens, with acoustic velocity less than that of superficial tissue, may be utilized, such as a liquid-filled lens, gel-filled or solid gel lens, rubber or composite lens, with adequate power handling capacity; or a concave-shaped, low profile, lens may be utilized and composed of any material or composite with velocity greater than that of tissue. While the structure of transducer source and configuration can facilitate a particular shaped lesion as suggested above, such structures are not limited to those particular shapes as the other spatial parameters, as well as the temporal parameters, can facilitate additional shapes within any transducer structure and source.

Through operation of ultrasound system 100, a method for treatment of cellulite can be realized that can facilitate effective and efficient therapy without creating chronic injury to human tissue. For example, a user may first select one or more transducer probe configurations for treating a region of interest. The user may select any probe configuration described herein. Because the treatment region ranges from approximately 0 mm to 3.5 cm, exemplary transducer probes may include, for example, an annular array, a variable depth transducer, a mechanically moveable transducer, a cylindrical-shaped transducer, a linear or flat transducer and the like. As used herein, the term user may include a person, employee, doctor, nurse, and/or technician, utilizing any hardware and/or software of other control systems.

Once one or more transducers are selected, the user may then image a region of interest in order to plan a treatment protocol. By imaging a region of interest, the user may user the same treatment transducer probe and/or one or more additional transducers to image the region of interest at a high resolution. In one embodiment, the transducer may be configured to facilitate high speed imaging over a large region of interest to enable accurate imaging over a large region of interest. In another embodiment, ultrasound imaging may include the use of Doppler flow monitoring and/or color flow monitoring. In addition other means of imaging such as photography and other visual optical methods, MRI, X-Ray, PET, infrared or others can be utilized separately or in combination for imaging and feedback of the superficial tissue and the vascular tissue in the region of interest.

Figure 12:
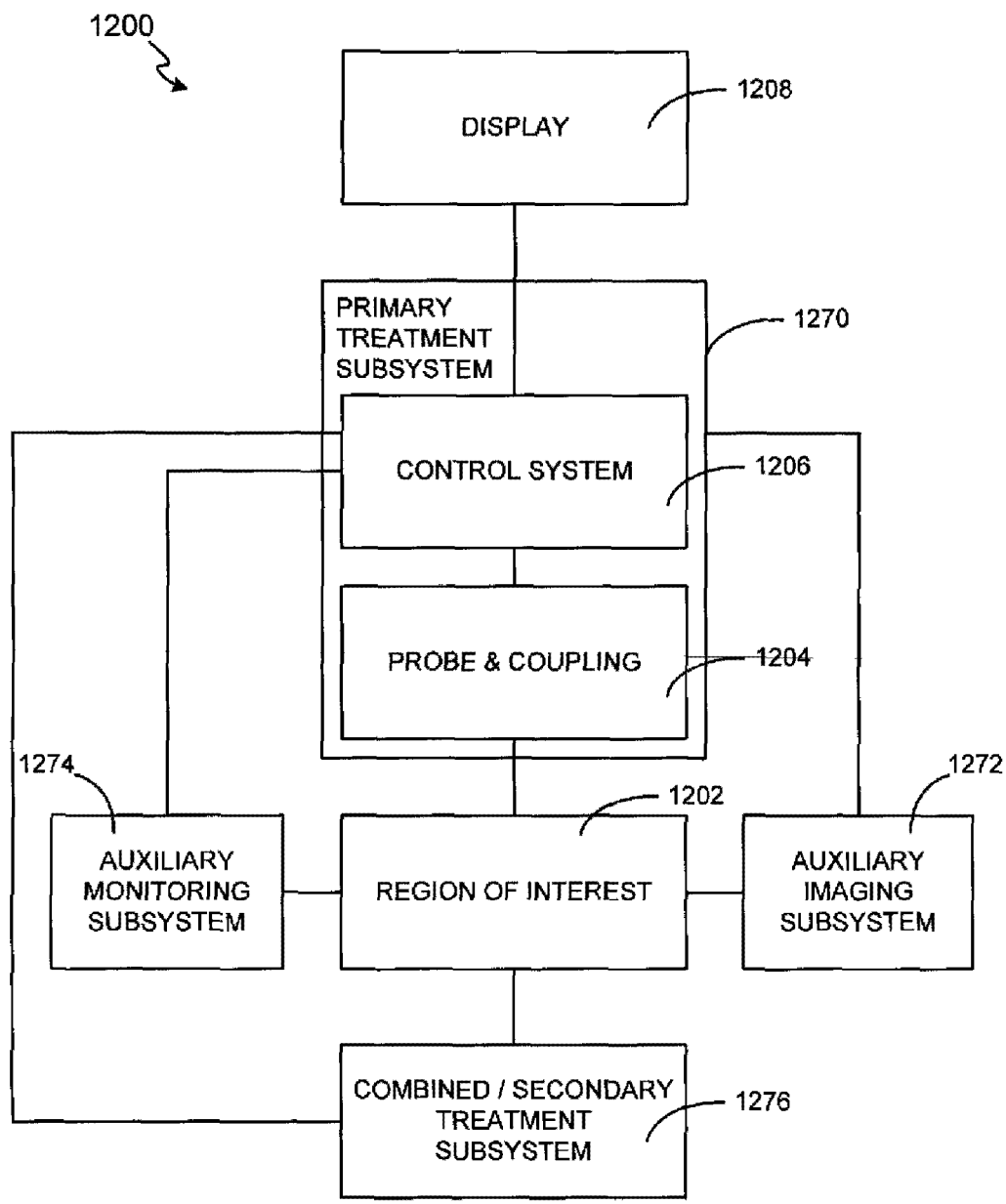
FIG. 12 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treating a region of interest 1206 can comprise a control system 1202, a probe 1204, and a display 1208. Treatment system 1200 further comprises an auxiliary imaging modality 1274 and/or auxiliary monitoring modality 1272 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of cellulite within region-of-interest 1206, including imaging/monitoring enhancements. Such imaging/monitoring enhancement for ultrasound imaging via probe 1204 and control system 1202 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF), intense pulsed light (IPL), laser, infrared laser, microwave, or any other suitable energy source.

Because the location and thickness of the fat lobuli varies from one patient to another (due to genetics, weight, age, etc.), imaging using a transducer can facilitate treatment within a patient, however imaging is not required to treat cellulite.

By planning a treatment protocol, the user may choose one or more spatial and/or temporal characteristics to provide conformal ultrasound energy to a region of interest. For example, the user may select one or more spatial characteristics to control, including, for example, the use one or more transducers, one or more mechanical and/or electronic focusing mechanisms, one or more transduction elements, one or more placement locations of the transducer relative to the region of interest, one or more feedback systems, one or more mechanical arms, one or more orientations of the transducer, one or more temperatures of treatment, one or more coupling mechanisms and/or the like.

In addition, the user may choose one or more temporal characteristics to control in order to facilitate treatment of the region of interest. For example, the user may select and/or vary the treatment time, frequency, power, energy, amplitude and/or the like in order to facilitate temporal control. For more information on selecting and controlling ultrasound spatial and temporal characteristics, see U.S. application Ser. No. 11/163,148, entitled "Method and System for Controlled Thermal Injury," filed Oct. 6, 2005 and previously incorporated herein by reference.

After planning of a treatment protocol is complete, the treatment protocol can be implemented. That is, a transducer system can be used to deliver ultrasound energy to a treatment region to ablate select tissue in order to facilitate cellulite treatment. By delivering energy, the transducer may be driven at a select frequency, a phased array may be driven with certain temporal and/or spatial distributions, a transducer may be configured with one or more transduction elements to provide focused, defocused and/or planar energy, and/or the transducer may be configured and/or driven in any other ways hereinafter devised.

In one exemplary embodiment, energy is delivered in relatively small ablative areas in order to minimize and/or prevent scar tissue from forming. That is, each ablative area of treatment can range from approximately 100 microns to 55 mm in diameter. In another exemplary embodiment, ultrasound energy is used in a "lawnmower" type fashion to evenly ablate a treatment region to provide a substantially planar surface of lobuli. This "lawnmower"-type ablation in turn, helps to achieve a substantially smooth surface of the epidermis.

In one exemplary embodiment, energy is delivered at a treatment depth of approximately 0 mm to 3.5 cm. The energy may range from 750 kHz to about 10 MHz, with typical applications ranging from 2 MHz to 10 MHz. In order to deliver energy in this treatment range, the transducer can be driven at power levels ranging from 20 W to 200 W. Because treatment time and treatment power are interrelated, these variables may differ from one patient to another and/or from one region of interest to another.

Once the treatment protocol has been implemented, the region of tissue may have one or more reactions to the treatment. For example, in one embodiment, the tissue responds by enhancement of lymphatic drainage, evacuation of fat decay products, creation of a thermal injury and/or coagulation of proximal protrusions of fat lobuli.

Upon treatment, the steps outlined above can be repeated one or more additional times to provide for optimal treatment results. Different ablation sizes and shapes may affect the recovery time and time between treatments. For example, in general, the larger the surface area of the treatment lesion, the faster the recovery. The series of treatments can also enable the user to tailor additional treatments in response to a patient's responses to the ultrasound treatment.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various steps may be deleted, modified, or combined with other steps. These and other changes or modifications are intended to be included within the scope of the present invention, as set forth in the following claims.

What is claimed is:

1. An ultrasound treatment device for treatment of cellulite, the device comprising:
   an ultrasound probe comprising a piezoelectric ultrasound therapy element and a motion mechanism,
   wherein a portion of the ultrasound probe is configured for acoustic coupling to a skin surface,
   wherein the piezoelectric ultrasound therapy element is configured for delivery of ultrasound energy at a temperature sufficient to coagulate at least a portion of a plurality of fat lobuli that protrude into a dermis layer to create an appearance of cellulite at a depth under the skin surface,
   wherein the piezoelectric ultrasound therapy element is connected to the motion mechanism,
   wherein the motion mechanism comprises an encoder configured to determine movement of the piezoelectric ultrasound therapy element,
   wherein the motion mechanism moves the piezoelectric ultrasound therapy element to form a plurality of thermal foci at the depth for coagulating fat thereby reducing an appearance of cellulite.

2. The device of claim 1,
   wherein the encoder is configured for monitoring a position of the piezoelectric ultrasound therapy element on the motion mechanism in a housing of the ultrasound probe,
   wherein the piezoelectric ultrasound therapy element is a single element that delivers the ultrasound energy at a frequency of between 2 MHz to 10 MHz,
   wherein the ultrasound energy is delivered with a treatment power of between 20 W and 200 W,
   wherein the piezoelectric ultrasound therapy element is configured to deliver the ultrasound energy at the depth below the skin surface,
   wherein the ultrasound energy generates a thermal lesion with a dimension of between 100 microns to 55 mm in the region of interest.

3. The device of claim 1, wherein the piezoelectric ultrasound therapy element is one of the group consisting of a spherically focused and a cylindrically focused.

4. The device of claim 1, further comprising a user control switch to activate the piezoelectric ultrasound therapy element and wherein the ultrasound energy increases a speed at which fat metabolizes according to Arrhenius Law: $Y = A \cdot e^{-B/T}$, where Y is a yield of metabolic reaction, A and B are constants, and T is a temperature in degrees Kelvin.

5. The device of claim 1, further comprising a control system comprising a processor, wherein the piezoelectric ultrasound therapy element is in communication with the control system, wherein the motion mechanism is in communication with the control system.

6. The device of claim 1, wherein the motion mechanism is a linear motion mechanism for linear movement of the piezoelectric ultrasound therapy element to form a plurality of thermal lesions along a line at the depth in the region of interest.

7. The device of claim 1, further comprising a piezoelectric ultrasound imaging element.

8. The device of claim 1, further comprising a piezoelectric ultrasound imaging element separate from, and co-housed with, the piezoelectric ultrasound therapy element in the probe.

9. The device of claim 1, wherein the motion mechanism is configured for any one of the group consisting of linear, rotational, and variable movement of the piezoelectric ultrasound therapy element.

10. An ultrasound device for treatment of cellulite, the device comprising:
    an ultrasound probe comprising a piezoelectric ultrasound therapy element, wherein a portion of the ultrasound probe is configured for acoustic coupling to a skin surface,
    wherein a plurality of fat lobuli protrude into a dermis layer under the skin surface,
    wherein the piezoelectric ultrasound therapy element is configured for communication with a control system,
    wherein the piezoelectric ultrasound therapy element is configured for delivery of energy at a temperature sufficient to coagulate at least a portion of the plurality of fat lobuli at a depth under the skin surface, thereby reducing an appearance of cellulite.

11. The device of claim 10,
    wherein the piezoelectric ultrasound therapy element is a single element that delivers ultrasound energy at a frequency of between 2 MHz to 10 MHz,
    wherein the ultrasound energy is delivered with a treatment power of between 20 W and 200 W,
    wherein the piezoelectric ultrasound therapy element is configured to deliver the ultrasound energy up to 3.5 cm below the skin surface,
    wherein the ultrasound energy generates a thermal lesion with a dimension of between 100 microns to 55 mm in the region of interest.

12. The device of claim 10,
    wherein the ultrasound probe comprises a housing, the housing containing a piezoelectric ultrasound imaging element,
    wherein the piezoelectric ultrasound imaging element is configured for imaging a region of interest under the skin surface, wherein the region of interest comprises a tissue, wherein the tissue comprises the plurality of fat lobuli.

13. The device of claim 10,
    wherein the piezoelectric ultrasound therapy element is a single element that delivers ultrasound energy at a frequency of between 750 kHz to 10 MHz, and wherein the ultrasound energy increases a speed at which fat metabolizes according to Arrhenius Law: $Y=A \cdot e^{-B/T}$, where Y is a yield of metabolic reaction, A and B are constants, and T is a temperature in degrees Kelvin.

14. The device of claim 10,
wherein the ultrasound probe is connected to a control system via a cable,
wherein the control system comprises: a processor, software, an input device, a power supply, and a communication device.

15. An ultrasound probe for treatment of cellulite, the probe comprising:
a housing, a piezoelectric ultrasound therapy element, and a motion mechanism,
wherein the piezoelectric ultrasound therapy element delivers ultrasound energy to a tissue below a skin surface at a frequency of between 2 MHz to 10 MHz,
wherein the tissue comprises a plurality of fat lobuli that protrude into a dermis layer to create an appearance of cellulite,
wherein the piezoelectric ultrasound therapy element is configured for delivery of the ultrasound energy at a temperature sufficient to coagulate at least a portion of a plurality of fat lobuli at a depth under the skin surface,
wherein the piezoelectric ultrasound therapy element is connected to the motion mechanism inside the housing,
wherein the motion mechanism comprises an encoder,
wherein the motion mechanism moves the piezoelectric ultrasound therapy element to form a plurality of thermal lesions at the depth for reducing an appearance of cellulite.

16. The probe of claim 15,
wherein the piezoelectric ultrasound therapy element is a single element,
wherein the piezoelectric ultrasound therapy element is configured to deliver the ultrasound energy at the depth below the skin surface, wherein the depth is a single, fixed depth,
wherein the ultrasound energy generates a thermal lesion with a dimension of between 100 microns to 55 mm in a region of interest.

17. The probe of claim 15, further comprising a control system that comprises a spatial control and a temporal control, the spatial control and the temporal control controlling the delivery of the ultrasound energy at a temperature sufficient to cause coagulation of at least the portion of the plurality of fat lobuli at the depth under the skin surface, wherein the ultrasound energy is delivered with a treatment power of between 20 W and 200 W.

18. The probe of claim 17, wherein the control system comprises: a processor; an input device; a power supply; and a communication device.

19. The probe of claim 15, further comprising a user control switch to activate the piezoelectric ultrasound therapy element and wherein the ultrasound energy increases a speed at which fat metabolizes according to Arrhenius Law: $Y=A \cdot e^{-B/T}$, where Y is a yield of metabolic reaction, A and B are constants, and T is a temperature in degrees Kelvin.

20. The probe of claim 15, wherein the piezoelectric ultrasound therapy element is configured to deliver the ultrasound energy at an energy level for causing at least one of ablating tissue, stretching fibrous bonds, or stimulating evacuation of fat decay products in the region of interest.

* * * * *